(12) United States Patent
Xu et al.

(10) Patent No.: US 11,355,217 B2
(45) Date of Patent: Jun. 7, 2022

(54) QUANTITATION AND MODELING OF QUALITY ATTRIBUTES OF THERAPEUTIC MONOCLONAL ANTIBODIES

(71) Applicant: Regeneron Pharmaceuticals, Inc., Tarrytown, NY (US)

(72) Inventors: Xiaobin Xu, White Plains, NY (US); Yu Huang, Ossining, NY (US)

(73) Assignee: Regeneran Pharmaceuticals, Inc., Tarrytown, NY (US)

( * ) Notice: Subject to any disclaimer, the term of this patent is extended or adjusted under 35 U.S.C. 154(b) by 594 days.

(21) Appl. No.: 16/264,044

(22) Filed: Jan. 31, 2019

(65) Prior Publication Data
US 2019/0237157 A1   Aug. 1, 2019

Related U.S. Application Data

(60) Provisional application No. 62/625,219, filed on Feb. 1, 2018.

(51) Int. Cl.
| | |
|---|---|
| *G01N 33/48* | (2006.01) |
| *G01N 33/50* | (2006.01) |
| *G16B 5/20* | (2019.01) |
| *G06F 17/11* | (2006.01) |
| *G01N 33/68* | (2006.01) |
| *C07K 16/00* | (2006.01) |
| *G16B 20/20* | (2019.01) |

(52) U.S. Cl.
CPC .......... *G16B 5/20* (2019.02); *G01N 33/6842* (2013.01); *G01N 33/6854* (2013.01); *G06F 17/11* (2013.01); *C07K 16/00* (2013.01); *C07K 2317/00* (2013.01); *G01N 2440/00* (2013.01); *G16B 20/20* (2019.02)

(58) Field of Classification Search
CPC .................................. G16B 5/20; G06F 17/11
See application file for complete search history.

(56) References Cited

U.S. PATENT DOCUMENTS

2002/0192223 A1* 12/2002 Hellstrom ........ G01N 33/57484
424/183.1

OTHER PUBLICATIONS

Alessandri et al. "Increased serum clearance of oligomannose species present on a human IgG1 molecule" mAbs vol. 4, No. 4:509-520; Jul./Aug. 2012; Landes Bioscience.

(Continued)

*Primary Examiner* — Russell S Negin
(74) *Attorney, Agent, or Firm* — Kramer Levin Naftalis & Frankel LLP

(57) ABSTRACT

Methods of predicting an in vivo serum concentration of an antibody with a post-translational modification of interest after administration of the antibody are provided, as are methods for predicting a subject's exposure to post-translational variants of the antibody. The methods include predicting a percentage of the antibody with the post-translational modification of interest using an in vivo rate constant determined for the post-translational modification, and multiplying the predicted percentage of the antibody with the post-translational modification of interest by the in vivo concentration of the antibody to determine the concentration of the antibody with the post-translational modification of interest.

11 Claims, 13 Drawing Sheets
Specification includes a Sequence Listing.

(56) References Cited

OTHER PUBLICATIONS

Athmer et al. "The Influence of Protein Structure on the Products Emerging from Succinimide Hydrolysis" The Journal of Biological Chemistry vol. 277, No. 34, Issue of Aug. 23; pp. 30502-30507 (2002).
Cai et al. "C-Terminal Lysine Processing of Human Immunoglobulin G2 Heavy Chain In Vivo" Biotechnology and Bioengineering vol. 108, No. 2:404-412; Feb. 2011.
Capasso et al. "Effect of the three-dimensional structure on the deamidation reaction of ribonuclease A" The Journal of Peptide Research: official journal of the American Peptide Society vol. 54:377-382 (1999).
Chelius et al. "Identification and Characterization of Deamidation Sites in the Conserved Regions of Human Immunoglobulin Gamma Antibodies" Analytical Chemistry vol. 77:6004-6011 (2005).
Delano et al. Convergent Solutions to Binding at a Protein-Protein Interface. Science vol. 287:1279-1284; Feb. 18, 2000.
Dick Jr. et al. "C-terminal Lysine Variants in Fully Human Monoclonal Antibodies: Investigation of Test Methods and Possible Causes" Biotechnology and Bioengineering vol. 100, No. 6:1132-1143 (Aug. 15, 2008).
Geiger et al. "Deamidation, Isomerization, and Racemization at Asparaginyl and Aspartyl Residues in Peptides" The Journal of Biological Chemistry vol. 262, No. 2, Issue of Jan. 15:785-794 (1987).
Goetze et al. "Assessing monoclonal antibody product quality attribute criticality through clinical studies" mAbs vol. 2 (No. 5):500-507 (Sep./Oct. 2010) Landes Bioscience.
Goetze et al. "High-mannose glycans on the Fc region of therapeutic IgG antibodies increase serum clearance in humans" Glycobiology vol. 21, No. 7:949-959 (2011).
Goetze et al. "Rates and impact of human antibody glycation in vivo" Glycobiology vol. 22, No. 2:221-234(2012).
Gu et al. "Characterization of trisulfide modification in antibodies" Analytical Biochemistry 400 (2010) 89-98.
Guidance for Industry, "Immunogenicity Assessment for Therapeutic Protein Products" U.S. Department of Health and Human Services; Aug. 2014; 39 pages.
Haberger et al. "Assessment of chemical modifications of sites in the CDRs of recombinant antibodies: Susceptibility vs. functionality of critical quality attributes" mAbs vol. 6, No. 2:327-339 (Mar./Apr. 2014); Landes Bioscience.
Huang et al. "In Vivo Deamidation Characterization of Monoclonal Antibody by LC/MS/MS" Analytical Chemistry vol. 77:1432-1439 (2005).
Kossiakoff. "Tertiary Structure is a Principal Determinant to Protein Deamidation" Science vol. 240:191-194 (1988).
Kozlowski et al. "Current and future issues in the manufacturing and development of monoclonal antibodies" Advanced Drug Delivery Reviews, vol. 58:707-722 (2006).
Li et al. "Quantitation and pharmacokinetic modeling of therapeutic antibody quality attributes in human studies" MABS vol. 8, No. 6:1079-1087 (2015).
Li, et al. "Assessing in vivo dynamics of multiple quality attributes from a therapeutic IgG4 monoclonal antibody circulating in cynomolgus monkey" MABS vol. 8, No. 5:961-968 (2016).
Liu et al. "Heterogeneity of Monoclonal Antibodies" Journal of Pharmaceutical Sciences, vol. 97:2426-2447 (2008).
Liu et al. "Human IgG2 antibody disulfide rearrangement in vivo" The Journal of Biological Chemistry vol. 283, No. 43:29266-29272; Oct. 24, 2008.
Liu et al. "N-terminal glutamate to pyroglutamate conversion in vivo for human IgG2 antibodies" The Journal of Biological Chemistry vol. 286, No. 13:11211-11217; Apr. 2011.

Mould et al. "The pharmacokinetics and pharmacodynamics of monoclonal antibodies—mechanistic modeling applied to drug development" Current Opinion in Drug Discovery & Development vol. 10, No. 1:84-96 (2007).
Ouellette et al. "Comparison of the in vitro and in vivo stability of a succinimide intermediate observed on a therapeutic IgG1 molecule" mAbs vol. 5:432-444; May/Jun. 2013; Landes Bioscience.
Pace et al. "Asparagine Deamidation Dependence on Buffer Type, pH, and Temperature" Journal of Pharmaceutical Sciences vol. 102, No. 6:1712-1723 (Jun. 2013).
Pan et al. "Methionine oxidation in human IgG2 Fc decreases binding affinities to protein A and FcRn" Protein Science: a publication of the Protein Society vol. 18:424-433 (2009).
Patel et al. "Chemical Pathways of Peptide Degradation. III. Effect of Primary Sequence on the Pathways of Deamidation of Asparaginyl Residues in Hexapeptides" Pharmaceutical Research, vol. 7 (No. 8):787-793 (1990).
Robinson et al. "Molecular Clocks" Proceedings of the National Academy of Sciences of the United States of America vol. 98, No. 3:944-949 (Jan. 30, 2001).
Robinson et al. "Structure-dependent nonenzymatic deamidation of glutaminyl and asparaginyl pentapeptides" The Journal of Peptide Research: official journal of the American Peptide Society vol. 63:426-436 (2004).
Rowland et al. Chapter 3 "Kinetics Following an Intravenous Bolus Dose" in Clinical Pharmacokinetics and Pharmacodynamics: Concepts and Applications, Wolters Kluwer Health/Lippincott William & Wilkins, 2011.
Schilling et al. "Glutaminyl cyclases from animals and plants: a case of functionally convergent protein evolution" Biological Chemistry, vol. 389:983-991 (Aug. 2008).
Sinha et al. "Effect of protein structure on deamidation rate in the Fc fragment of an IgG1 monoclonal antibody" Protein Science vol. 18:1573-1584 (2009).
Song et al. "Effect of 'pH' on the rate of asparagine deamidation in polymeric formulations: 'pH'—rate profile" Journal of Pharmaceutical Sciences, vol. 90:141-156 (2001).
Stephenson et al. "Succinimide Dormation from Aspartyl and Asparaginyl Aeptides as a Model for the Spontaneous Degradation of Proteins" The Journal of Biological Chemistry vol. 264, No. 11, Issue of Apr. 15; pp. 6164-6170 (1989).
Wakankar et al. "Formulation Considerations for Proteins Susceptible to Asparagine Deamidation and Aspartate Isomerization" Journal of Pharmaceutical Sciences, vol. 95:2321-2336 (2006).
Wang et al. "Antibody Structure, Instability, and Formulation" Journal of Pharmaceutical Sciences vol. 96, No. 1 (Jan. 2007).
Wearne et al. "Effect of Protein Conformation on Rate of Deamidation: Ribonuclease A" Proteins, vol. 5:8-12 (1989).
Xie et al. "Secondary Structure and Protein Deamidation" Journal of Pharmaceutical Sciences, vol. 88:8-13(1999).
Xu et al. "LC-MS multi-attribute method for characterization of biologies" Journal of Applied Bioanalysis vol. 3, No. 2: 21-25; Apr. 2017.
Xu. "In vivo characterization of therapeutic monoclonal antibodies" Journal of Applied Bioanalysis vol. 2, No. 1:10-15; Jan. 2016.
Yan et al. "Succinimide formation at Asn 55 in the complementarity determining region of a recombinant monoclonal antibody IgG1 heavy chain" Journal of Pharmaceutical Sciences, vol. 98:3509-3521 (2009).
Yin et al. "Characterization of Therapeutic Monoclonal Antibodies Reveals Differences Between In Vitro and n Vivo Time-Course Studies" Pharmaceutical Research vol. 30:167-178 (2013).
Zheng et al. "Influence of pH, buffer species, and storage temperature on physicochemical stability of a humanized monoclonal antibody LA298" International Journal of Pharmaceutics vol. 308:46-51 (2006).

* cited by examiner

SEQUENCE LISTING

<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Met oxidized peptide

<400> SEQUENCE: 1

Asp Thr Leu Met Ile Ser Arg
1               5

QUANTITATION AND MODELING OF QUALITY ATTRIBUTES OF THERAPEUTIC MONOCLONAL ANTIBODIES

CROSS-REFERENCE TO RELATED APPLICATIONS

This application claims the benefit under 35 USC § 119(e) of U.S. Provisional Application No. 62/625,219, filed Feb. 1, 2018, which is herein specifically incorporated by reference in its entirety.

SEQUENCE LISTING

This application incorporates by reference the Sequence Listing submitted in Computer Readable Form as 10421US01-Sequence.txt, created on Jan. 31, 2019 and containing 514 bytes.

FIELD OF THE INVENTION

The present invention pertains to biopharmaceuticals, and relates to the prediction and modeling of in vivo post-translational modifications of therapeutic antibodies.

BACKGROUND

Therapeutic monoclonal antibodies (mAbs) are heterogeneous molecules produced in mammalian cells with many product variants, including variants resulting from post-translational modifications (PTMs). Variants produced via PTMs can occur throughout the lifespan of a mAb during production, purification, storage, and post-administration. These variants or product-related modifications are also referred to as product quality attributes (PQAs). Controlling PQAs within predefined acceptance criteria is vital to the biopharmaceutical industry because it ensures consistent product quality and reduces potential impacts on drug safety and efficacy. The modifications that occur during drug production and storage can often be reliably monitored and controlled. However, additional modifications can occur after drug administration due to the remarkably different environments of the blood stream versus formulation buffers. In vivo modifications of mAbs are usually difficult to monitor and less often studied. Assessment and prediction of PTM changes in vivo would not only facilitate the understanding of quality attribute criticality for product risk assessment, but would also help product design and development teams engineer mAb drug candidates with enhanced in vivo stability.

A Food and Drug Administration guidance for industry recommends that sponsors should evaluate susceptibilities of therapeutic proteins to modifications within the in vivo milieu (see, Guidance for Industry, Immunogenicity Assessment for Therapeutic Protein Products. 2014). As a result, in vivo behavior of many PQAs, including deamidation (see, for example, Huang et al., Analytical chemistry 2005; 77:1432-9; Ouellette et al., mAbs 2013; 5:432-44; Yin et al., Pharmaceutical research 2013; 30:167-78; Li et al., mAbs 2016:0; Li et al., mAbs 2016:0), oxidation (see, for example, Yin et al., Pharmaceutical research 2013; 30:167-78; Li et al., mAbs 2016:0; Li et al., mAbs 2016:0), glycation (see, for example, Goetze et al., Glycobiology 2012; 22:221-34), glycosylation (see, for example, Li et al., mAbs 2016:0; Li et al., mAbs 2016:0; Goetze et al., Glycobiology 2011; 21:949-59; Alessandri et al., mAbs 2012; 4:509-20), disulfides (see, for example, Li Y et al., mAbs 2016:0; Liu et al., The Journal of biological chemistry 2008; 283:29266-72), N-terminal pyroglutamate (see, for example, Yin et al., Pharmaceutical research 2013; 30:167-78; Li et al., mAbs 2016:0; Li et al., mAbs 2016:0; Liu et al., The Journal of biological chemistry 2011; 286:11211-7), and C-terminal lysine removal (see, for example, Li et al., mAbs 2016:0; Cai et al., Biotechnology and bioengineering 2011; 108:404-12) have been investigated in animal or human samples. Affinity purification is often used to extract the therapeutic mAb from serum samples to reduce the interference of endogenous protein background in analysis (see, for example, Li et al., mAbs 2016:0; Li et al., mAbs 2016:0). For studies in animals, an anti-human Fc antibody or an antigen can be readily used as a capture reagent; for human studies, an antigen or an antibody that specifically recognizes the unique complementarity-determining region (CDR) of the therapeutic mAb can be used as a capture reagent. After affinity purification, liquid chromatography tandem mass spectrometry (LC-MS/MS) peptide mapping is often used to quantitate the relative abundance of PTM product variants. Recently, in vivo PTM quantitation has been combined with pharmacokinetic (PK) models to evaluate the formation and elimination of PTM product variants and quantitatively assess the subject's exposure to PQAs in single-dose regimens (see, for example, Li et al., mAbs 2016:0; Li et al., mAbs 2016:0; Goetze et al., mAbs 2010; 2:500-7) to help establish the criticality of PQAs for product risk assessment. However, modeling that simulates the in vivo progression of PTMs and subject's exposure to PQAs to quantitatively assess criticality of the PQAs in multiple-dose regimens has not been attempted.

SUMMARY OF THE INVENTION

In one aspect, the present invention provides a method of predicting an in vivo serum concentration of an antibody with a post-translational modification of interest after a single administration of the antibody, in which the method comprises (a) predicting a percentage of the antibody with the post-translational modification of interest using an in vivo rate constant determined for the post-translational modification; and (b) multiplying the predicted percentage of the antibody with the post-translational modification of interest by the in vivo concentration of the antibody to determine the concentration of the antibody with the post-translational modification of interest. In some cases, the following equation is employed in the calculations: $C_{PTM}(t) = C(t) \cdot P(t)$, where $C_{PTM}(t)$ is the serum concentration of the antibody with the post-translational modification of interest; $C(t)$ is the serum concentration of the antibody; and $P(t)$ is the percentage of the post-translational modification of interest.

In some embodiments, the in vivo rate constant for the post-translational modification is determined by quantitating a percentage of the post-translational modification of interest as a function of time and fitting the quantitated percentage of the post-translational modification of interest to the equation $P_{PTM}(t) = 1 - (1 - P_0) \cdot e^{-k_{PTM} t}$, where $P_{PTM}(t)$ is the proportion of the post-translational modification as a function of time; $P_0$ is an initial percentage post-translational modification; and $k_{PTM}$ is the post-translational modification rate constant.

In some embodiments, the method further comprises determining the exposure of the subject to the antibody with the post-translational modification of interest. In some cases, determining the exposure of the subject to the antibody with the post-translational modification of interest includes determining the area under the curve (AUC) of the concentration ($C_{PTM}(t)$) of the antibody with the post-translational modification of interest.

In some embodiments, the serum concentration of the antibody is described by a two-compartment pharmacokinetic model equation as $C(t)=Ae^{-\alpha t}+Be^{-\beta t}$, where A and B are hybrid coefficients when $\alpha$ and $\beta$ are hybrid first order constants, respectively.

In some embodiments, the method further comprises predicting the in vivo serum concentration of the antibody with the post-translational modification of interest after multiple administrations of the antibody. In some cases, predicting the in vivo serum concentration of the antibody with the post-translational modification of interest after multiple administrations of the antibody comprises superimposing multiple single administration models, wherein the serum concentration of the antibody at each administration is described individually by a two-compartment pharmacokinetic model equation as $C(t)=Ae^{-\alpha t}+Be^{-\beta t}$, where A and B are hybrid coefficients when $\alpha$ and $\beta$ are hybrid first order constants, respectively.

In various embodiments of the method, the antibody comprises a recombinant therapeutic monoclonal antibody. In some cases, the post-translational modification comprises a product quality attribute that can impact drug stability, safety, and/or efficacy.

In some embodiments, the method predictively monitors the post-translational modification profile of a monoclonal antibody.

In some embodiments, the method further comprises creating a predictive model of the in vivo progression of post-translational modifications and a subject's exposure to product quality attributes.

In some embodiments, the method further comprises modeling a correlation between PK concentration and proportion of post-translational modification variants.

In some embodiments, the method further comprises quantitatively assessing and predicting the subject exposure to a representative post-translational modification in both single- and multiple-dose regimens.

In some embodiments, the method further comprises predicting the maximum and minimum post-translational modification levels observed in the multiple-dose regimens.

In another aspect, the present invention provides a method for predicting exposure of a subject to a variant of a recombinant therapeutic monoclonal antibody following administration to the subject, in which the method comprises (a) identifying a rate constant for a post-translational modification (PTM) process that causes formation of the variant; (b) calculating a predicted proportion of the variant as a function of time; (c) calculating a predicted serum concentration of the variant in the subject as a function of time based on the predicted proportion of the variant; and (d) predicting exposure of the subject to the variant following administration of the antibody based on the predicted serum concentration of the variant.

In some embodiments of the method, calculating the predicted proportion of the variant as a function of time is performed via the following equation: $P_{PTM}(t)=1-(1-P_0)\cdot e^{-k_{PTM}t}$, wherein $P_{PTM}(t)$ is the proportion of the variant as a function of time, $P_0$ is the initial level of the variant at the time of administration, $k_{PTM}$ is the rate constant for the PTM process, and t is time.

In some embodiments of the method, calculating the predicted serum concentration of the variant in the subject as a function of time is performed via the following equation: $C_{PTM}(t)=C(t) P_{PTM}(t)$, wherein $C_{PTM}(t)$ is the serum concentration of the variant, $C(t)$ is the serum concentration of the antibody, and $P_{PTM}(t)$ is the proportion of the variant at time t.

In some embodiments, the method further comprises administering the antibody to the subject.

In some embodiments of the method, the antibody is a mAb.

In some embodiments, the method further comprises determining the total in vivo concentration of the antibody in the subject.

In another aspect, the present invention provides a method for predicting exposure of a subject to a variant of a recombinant therapeutic monoclonal antibody following administration of multiple doses of the antibody to the subject, in which the method comprises (a) performing the method discussed directly above; (b) calculating the predicted proportion of the variant prior to and after each subsequent dose of the antibody based on a dosing interval; (c) calculating the predicted serum concentration of the variant in the subject based on the predicted proportion of the variant at each dosing interval; and (d) predicting exposure of the subject to the variant over the course of two or more doses of the antibody based on the predicted serum concentration of the variant.

In various embodiments of the methods discussed above or herein, the post-translational modification comprises one or more of deamidation, oxidation, glycation, disulfide formation, N-terminal pyroglutamate formation, C-terminal lysine removal, and high mannose glycosylation.

In some embodiments, the method further comprises administering the antibody to the subject.

In some embodiments of the method, the antibody is a mAb.

In some embodiments, the method further comprises determining the a total in vivo concentration of the antibody in the subject.

Any of the various aspects or embodiments discussed above or herein may be combined in alternative embodiments, each of which is encompassed within the scope of the present disclosure.

DESCRIPTION OF THE FIGURES

(FIG. 2A) The MS/MS spectrum of an example Met oxidized peptide, DTLMISR (SEQ ID NO: 1) (top panel) and the MS/MS spectrum of the example wild-type peptide, DTLMISR (SEQ ID NO: 1) (bottom panel). (FIG. 2B) Extracted ion chromatograph of the Met oxidized peptide, DTLMISR (SEQ ID NO: 1) (top panel) and the wild-type peptide, DTLMISR (SEQ ID NO: 1) (bottom panel).

(FIG. 3A) In the single-dose study, the relative abundance of deamidation at each of the three Asn sites increased over time at different rates following the first-order kinetic equation: $P_{deam}(t)=1-(1-P_0)\cdot e^{k_{deam}t}$. Using non-linear regression, the in vivo deamidation rate constants at Asn site 1, 2, and 3 were determined to be 0.003523% day-1, 0.5394% day-1, and 0.1546% day-1, respectively. (Figure B) In the multiple-dose study, the relative abundance of deamidation at each of the three Asn sites increased over time during each dosing interval following the first-order kinetic equation, but decreased sharply following each subsequent dose due to dilution with newly administered unmodified MAB1, exhibiting an upward trending saw-tooth pattern. Each dosing time is indicated with an arrow "↑".

(FIG. 4A) In the single-dose study, the relative abundance of Met oxidation fluctuated slightly but remained nearly unchanged at all three sites. (FIG. 4B) In the multiple-dose study, the relative abundance of oxidation at Met site 1 decreased slightly during each dosing interval and increased slightly after each dose. The relative abundances of oxidation at Met site 2 and 3 remained stable. Each dosing time is indicated with an arrow "↑".

(FIG. 5A) In the single-dose study, the relative abundance of N-terminal pyroglutamate increased over time. (FIG. 5B) In the multiple-dose study, the relative abundance of N-terminal pyroglutamate increased during each dosing interval but decreased sharply following each subsequent dose of MAB1 due to dilution with newly administered unmodified MAB1, exhibiting an upward trending saw-tooth pattern. Each dosing time is indicated with an arrow "↑".

(FIG. 7A) In the single-dose study, the relative abundance of Mannose 5 decreased from 0.5% to undetectable within 6 weeks. (FIG. 7B) In the multiple-dose study, the relative abundance of Mannose 5 decreased during each dosing interval but sharply increased at each subsequent new dose because of newly administered MAB1 with a higher level of Mannose 5, exhibiting a downward trending saw-tooth pattern. Each dosing time is indicated with an arrow "↑".

(FIG. 11A) The subject's exposure to the hypothetical CDR deamidated variants with 0%, 10%, and 20% initial deamidation over 56 days in the single-dose study are 1385 μg/mL·day, 1653 μg/mL·day, and 1921 μg/mL·day, respectively, consisting of 32.5%, 38.8%, and 45.1% subject's exposure to the total mAb, respectively. (FIG. 11B) The subject's exposure to the hypothetical CDR deamidated variants with 0%, 10%, and 20% initial deamidation over 5 doses (56 days) in the multiple-dose study are 1086 μg/mL·day, 1478 μg/mL·day, and 1871 μg/mL·day, respectively, consisting of 21.7%, 29.5%, and 37.3% subject's exposure to the total mAb, respectively Each dosing time is indicated with an arrow "↑".

DETAILED DESCRIPTION OF THE INVENTION

Figure 1:
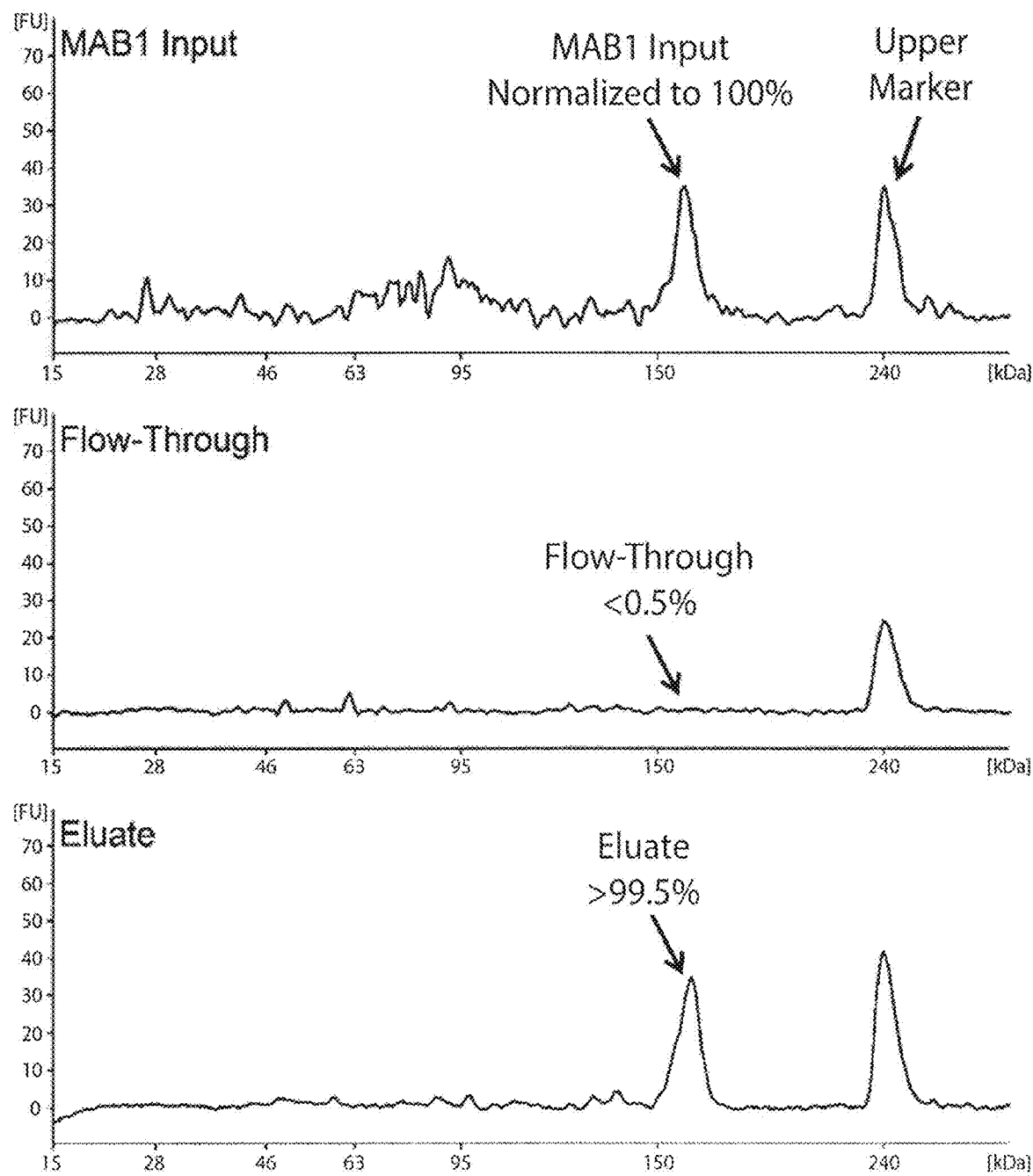
FIG. 1 is a set of traces showing the recovery of MAB1 protein by affinity purification. The recovery rate of the affinity purification of MAB1 was >99.5% while <0.5% total MAB1 was detected in the flow-through. The calculation of percent recovery rate was described in the Materials and Methods section of Example 1. A known amount of high molecular-weight standard (shown as "Upper Marker") was run with each sample as an internal normalization control. The ratio of the MAB1 peak area to the Upper Marker peak area in each sample was calculated to correct for run-to-run variability.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All patents, applications and non-patent publications mentioned in this specification are incorporated herein by reference in their entireties.

Abbreviations Used Herein

Asn: Asparagine
AUC: Area Under Curve
CDR: Complementarity-Determining Region
CV: Coefficient of Variations
EIC: Extracted Ion Chromatograph
ELISA: Enzyme-Linked Immunosorbent Assay
FDA: Food and Drug Administration
HC: Heavy Chain
IgG: Immunoglobulin G
LC: Light Chain
mAb: Monoclonal Antibody
MAB1: the therapeutic human monoclonal antibody used in Example 1
Met: Methionine
PK: Pharmacokinetics
PQA: Product Quality Attribute
PTM: Post-Translational Modification
RP-LC-MS/MS: Reversed Phase Liquid Chromatography Tandem Mass Spectrometry

Definitions

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). In various embodiments, the heavy chain may be an IgG isotype. In some cases, the heavy chain is selected from IgG1, IgG2, IgG3 or IgG4. In some embodiments, the heavy chain is of isotype IgG1 or IgG4, optionally including a chimeric hinge region of isotype IgG1/IgG2 or IgG4/IgG2. Each light chain is comprised of a light chain variable region ("LCVR or "$V_L$") and a light chain constant region (CL). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" includes antibody molecules prepared, expressed, created or isolated by recombinant means, such as antibodies isolated from a host cell transfected to express the antibody. For a review on antibody structure, see Lefranc et al., *IMGT unique numbering for immunoglobulin and T cell receptor variable domains and Ig superfamily V-like domains*, 27(1) Dev. Comp. Immunol. 55-77 (2003); and M. Potter, *Structural correlates of immunoglobulin diversity*, 2(1) Surv. Immunol. Res. 27-42 (1983).

The term antibody also encompasses "bispecific antibody", which includes a heterotetrameric immunoglobulin that can bind to more than one different epitope. One half of the bispecific antibody, which includes a single heavy chain and a single light chain and six CDRs, binds to one antigen or epitope, and the other half of the antibody binds to a different antigen or epitope. In some cases, the bispecific antibody can bind the same antigen, but at different epitopes or non-overlapping epitopes. In some cases, both halves of the bispecific antibody have identical light chains while retaining dual specificity. Bispecific antibodies are described generally in U.S. Patent App. Pub. No. 2010/0331527 (Dec. 30, 2010).

The term "antigen-binding portion" of an antibody (or "antibody fragment"), refers to one or more fragments of an antibody that retain the ability to specifically bind to an antigen. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 241:544-546), which consists of a VH domain, (vi) an isolated CDR, and (vii) an scFv, which consists of the two domains of the Fv fragment, VL and VH, joined by a synthetic linker to form a single protein chain in which the VL and VH regions pair to form monovalent molecules. Other forms of single chain antibodies, such as diabodies are also encompassed under the term "antibody" (see e.g., Holliger et at. (1993) 90 PNAS U.S.A. 6444-6448; and Poljak et at. (1994) 2 Structure 1121-1123).

Moreover, antibodies and antigen-binding fragments thereof can be obtained using standard recombinant DNA techniques commonly known in the art (see Sambrook et al., 1989).

"Fc fusion proteins" comprise part or all of two or more proteins, one of which is an Fc portion of an immunoglobulin molecule, which are not otherwise found together in nature. Preparation of fusion proteins comprising certain heterologous polypeptides fused to various portions of antibody-derived polypeptides (including the Fc domain) has been described, e.g., by Ashkenazi et at., (1991) 88 Proc. Natl. Acad. Sci. U.S.A. 10535; Byrn et at., (1990) 344 Nature 677; and Hollenbaugh et at., (1992) "Construction of Immunoglobulin Fusion Proteins", in Current Protocols in Immunology, Suppl. 4, pages 10.19.1-10.19.11. "Receptor Fc fusion proteins" comprise one or more extracellular domain(s) of a receptor coupled to an Fc moiety, which in some embodiments comprises a hinge region followed by a CH2 and CH3 domain of an immunoglobulin. In some embodiments, the Fc-fusion protein contains two or more distinct receptor chains that bind to one or more ligand(s). For example, Fc-fusion protein is a trap, such as for example an IL-1 trap (e.g., rilonacept, which contains the IL-1RAcP ligand binding region fused to the IL-1R1 extracellular region fused to Fc of hIgG1; see U.S. Pat. No. 6,927,004), or a VEGF trap (e.g., aflibercept, which contains the Ig domain 2 of the VEGF receptor Flt1 fused to the Ig domain 3 of the VEGF receptor Flk1 fused to Fc of hIgG1; see U.S. Pat. No. 7,087,411 (issued Aug. 8, 2006) and U.S. Pat. No. 7,279,159 (issued Oct. 9, 2007)).

The term "human antibody", is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

As used herein, the term "subject" refers to an animal, preferably a mammal, more preferably a human, for example in need of amelioration, prevention and/or treatment of a disease or disorder.

As used herein, the terms "treat", "treating", or "treatment" refer to the reduction or amelioration of the severity of at least one symptom or indication due to the administration of a therapeutic agent such as an antibody of the present invention to a subject in need thereof. The terms include inhibition of progression of disease. The therapeutic agent may be administered at a therapeutic dose to the subject.

A "post-translational modification" (PTM) refers to the covalent modification of proteins following protein biosynthesis. Post-translational modifications can occur on the amino acid side chains or at the protein's C- or N-termini. Exemplary post-translational modifications of antibodies include deamidation, oxidation, glycation, disulfide formation, N-terminal pyroglutamate formation, C-terminal lysine removal, and glycosylation.

General Description

Therapeutic monoclonal antibodies (mAbs) produced in mammalian cells are heterogeneous as a result of post-translational modifications (PTMs). PTMs of therapeutic monoclonal antibodies (mAbs) are important product quality attributes (PQAs) that can potentially impact drug stability, safety, and efficacy (Xu et al., Journal of Applied Bioanalysis 2017; 3:21-5). PTMs can occur during mAb production, purification, storage, and post-administration (Kozlowski et al., Advanced drug delivery reviews 2006; 58:707-22; Liu et al., Journal of pharmaceutical sciences 2008; 97:2426-47; Goetze et al., mAbs 2010; 2:500-7; Wang et al., Journal of pharmaceutical sciences 2007; 96:1-26). The modifications that occur during drug production and storage can be reliably monitored and controlled. However, additional modifications may occur after drug administration as a result of the different environments encountered by mAbs in vivo versus in vitro. The PTMs of a mAb changes remarkably after administration into the bloodstream compared to in vitro conditions. Thus, monitoring in vivo PTM changes of mAbs helps evaluate the criticality of PQAs during product risk assessment. In addition, quantitative assessment of a subject's exposure to PTM variants helps assess the impact of PTMs on the safety and efficacy of therapeutic mAbs. Assessment and prediction of PTMs that can occur in vivo not only facilitate the understanding of quality attribute criticality for product risk assessment, but also help product development teams to engineer mAb drug candidates with enhanced in vivo stability.

As disclosed herein, the inventors have undertaken a detailed analysis and determination of product quality attributes (PQAs) that are present in therapeutic monoclonal antibodies. Using the therapeutic monoclonal antibody MAB1 as a model, the inventors have assessed a number of post-translation modifications, including, for example, deamidation, oxidation, N-terminal pyroglutamate formation, and C-terminal lysine removal. As disclosed herein the inventors determined PTMs (e.g., deamidation, oxidation, N-terminal pyroglutamate formation, C-terminal lysine removal, and high mannose glycosylation) of a therapeutic mAb, MAB1, in single- and multiple-dose monkey pharmacokinetic (PK) studies. Using the data obtained, the inventors built modeling equations to calculate the in vivo serum concentrations of PQAs, the subject's exposure to PQAs, and the relative abundance of PQAs in single- and multiple-dose regimens using three common PTMs as examples. The model predictions demonstrated agreement with the experimental results. An example application of the models was elucidated using a hypothetical PTM. The models provide bioanalytical chemists with a simplified modeling tool to quantitatively assess the criticality of PQAs when advanced PK models are not available. As detailed in the Example below, monkey serum samples from single- and multiple-dose PK studies were analyzed with affinity purification followed by LC-MS/MS, to determine a number of post-translational attributes of MAB1. Using the data obtained from this analysis, the inventors were able to construct a mathematical model and/or simulation of the in vivo progression of antibody post-translational modifications to predict a subject's exposure to product quality attributes of a therapeutic antibody. The simulation provides a quantitative approach to assess the criticality of the PQAs.

Based on a single-dose PK study of the PQAs of MAB1, the inventors were able to model PK concentration and proportion of PTM variants, and to quantitatively assess and predict the subject's exposure to a representative PTM attribute (for example, asparagine deamidation) in both single- and multiple-dose regimens. The model also predicted the maximum and minimum PTM levels observed in the multiple-dose regimens. This modeling approach provides a new tool for bioanalytical chemists to quantitatively assess the criticality of PQAs in therapeutic mAbs. The models could be used to evaluate the impact of the PQAs caused by process changes or lot-to-lot variability by adjusting the initial PQA levels ($P_0$). If the modeling demonstrated that the progression of a PQA or the subject's exposure to the PQA is insensitive to the initial levels of PQAs, the acceptable ranges of the PQA could be widened to adopt the process changes.

The models could also be used to simulate the subject's exposure by extending the dosing period (t) or changing the dosing interval ($\tau$), providing a quantitative assessment of the subject's exposure to PQAs in pre-clinical and clinical studies. Quantitative assessment of the subject's exposure to a PQA could help evaluate the risks associated with the PQA. A PQA with known adverse immunological reactions that has been determined to have a high exposure level during PK studies would have high potential risk. In such cases, certain strategies (e.g. protein re-engineering to enhance the in vivo stability) could be implemented to eliminate or reduce the level of the PQA.

Method of Prediction of Exposure to Antibody Product Quality Attributes

Disclosed herein is a method of predicting an in vivo serum concentration of an antibody with a post-translational modification of interest after administration of the antibody (such as a therapeutic monoclonal antibody) to a subject. The disclosed method includes predicting a percentage of the antibody with the post-translational modification of interest using an in vivo rate constant determined for the post-translational modification of interest. The percentage of the antibody with the post-translational modification can be multiplied by the total in vivo concentration of the antibody at any time point to determine the concentration of the antibody with the post-translational modification of interest at that time point. For example, using the equation $C_{PTM}(t) = C(t) \cdot P(t)$, where $C(t)$ is the serum concentration of the antibody; and $P(t)$ is the percentage of the post-translational modification of interest. The serum concentration ($C_{PTM}(t)$) of the antibody with the post-translational modification of interest can be determined. In other words, the serum concentration of the antibody with the post-translational modification of interest is the percentage of total antibody having that post-translational modification. As disclosed herein, the serum concentration of the antibody may be described by the two-compartment pharmacokinetic model equation as $C(t) = Ae^{-\alpha t} + Be^{-\beta t}$, where A and B are hybrid coefficients when $\alpha$ and $\beta$ are hybrid first order constants, respectively.

In embodiments, the in vivo rate constant for the post-translational modification of interest is determined by quantitating a percentage of the post-translational modification of interest as a function of time after a single dose and fitting the quantitated percentage of the post-translational modification of interest to the equation $P_{PTM}(t) = 1 - (1-P_0) \cdot e^{-k_{PTM} t}$, where $P_{PTM}(t)$ is the proportion of the post-translational modification of interest as a function of time; $P_0$ is an initial percentage post-translational modification of interest; and $k_{PTM}$ is the post-translational modification rate constant for the post-translational modification of interest. By fitting the curve to the measured percentage of the post-translational modification of interest the rate constant $k_{PTM}$ can be determined, for example using non-linear regression or other mathematical fitting algorithms.

In embodiments, the method can also include determining the exposure of the subject to the amount of antibody with the post-translational modification of interest. For example, using area under the curve (AUC) analyses of the concentration ($C_{PTM}(t)$) of the antibody with the post-translational modification of interest over a time period of interest, for example days, weeks or even months, yields a value for the total exposure of the subject to the amount of antibody having the post-translational modification of interest.

Looking at multiple sites simultaneously is also possible. For example the proportion of an antibody with a post-translational modification at a certain site can be described by first order kinetics, as $P_{PTM\_site\_i}(t) = 1-(1-P_{PTM\_site\_i}) \cdot e^{-k_{PTM\_site\_i} t}$, where $P_{PTM\_site\_i}(t)$ is the proportion of the post-translational modification at a site i as a function of time; $P_0$ is the initial post-translational modification level that site i; $k_{PTM\_site\_i}$ is the post-translational modification rate constant at site i. Therefore, the PK concentration of antibody with a certain site i within the antibody post translationally modified can be described as $C_{PTM\_site\_i}(t) = C(t) \cdot P_{PTM\_site\_i}(t)$. The area under the curve (AUC) of $C_{PTM\_site\_i}(t)$ plot presents the subject's exposure to a quality attribute. One can further calculate the approximate concentration of each species of antibody variant, for example having 1, 2, 3, or even more distinct post-translational modifications.

As discussed in the Example below with respect to deamidation, by extending the model to multiple administrations, the method disclosed herein may be used to predict the in vivo serum concentration of an antibody with the post-translational modification of interest after multiple administrations of the antibody. For example, predicting the in vivo serum concentration of an antibody with the post-translational modification of interest after multiple administrations of the antibody can include superimposing multiple single administration models, wherein the serum concentration of the antibody at each administration is described individually by a two-compartment pharmacokinetic model equation as $C(t) = Ae^{-\alpha t} + Be^{-\beta t}$, where A and B are hybrid coefficients when $\alpha$ and $\beta$ are hybrid first order constants, respectively.

The serum concentration of an antibody with post-translational modification of interest immediately before the $m^{th}$ dose can be described as follows:

$$C_{PTM,m,pre\text{-}dose}(m \cdot \tau) = P_{PTM}[(m-1) \cdot \tau] C[(m-1) \cdot \tau] + \ldots + P_{PTM}(1 \cdot \tau) C(1 \cdot \tau)$$

The serum concentration of an antibody with post-translational modification of interest immediately after the $m^{th}$ dose can be described as follows:

$$C_{PTM,m,post\text{-}dose}(m \cdot \tau) = P_{PTM}[(m-1) \cdot \tau] C[(m-1) \cdot \tau] + \ldots + P_{PTM}(1 \cdot \tau) C(1 \cdot \tau) + P_{PTM}(0) C(0)$$

where $P_{PTM}(t)$ is the first order reaction equation, as described for a single administration. Thus, the proportion of antibody with a post-translational modification of interest immediately before the $m^{th}$ dose can be described as follows:

$$P_{PTM,m,pre\text{-}dose}(m \cdot \tau) = \frac{C_{PTM,m,pre\text{-}dose}(m \cdot \tau)}{C_{m,pre\text{-}dose}(m \cdot \tau)}$$

The proportion of antibody with a post-translational modification of interest immediately after the $m^{th}$ dose can be described as follows:

$$P_{PTM,m,post\text{-}dose}(m \cdot \tau) = \frac{C_{PTM,m,post\text{-}dose}(m \cdot \tau)}{C_{m,post\text{-}dose}(m \cdot \tau)}$$

When m approaches infinity, the $P_{deam,m,pre\text{-}dose}$ and $P_{PTM,m,after\text{-}dose}$ reach a plateau, which can be described as follows:

$$P_{PTM,\infty,pre\text{-}dose} = \frac{1}{C_{\infty,pre\text{-}dose}} \sum_{i=1}^{\infty} P_{deam}(i) \cdot C(i) =$$

-continued $$\frac{1}{C_{\infty,pre-dose}}\sum_{i=1}^{\infty}[1-(1-P_0)e^{-k\tau i}](A\cdot e^{-\alpha\tau i}+B\cdot e^{-\beta\tau i})$$

Therefore:

$$P_{PTM,\infty,pre-dose} = \frac{A\left(\frac{1}{e^{\alpha\tau}-1}-\frac{1-P_0}{e^{(\alpha+k)\tau}-1}\right)+B\left(\frac{1}{e^{\alpha\tau}-1}-\frac{1-P_0}{e^{(\beta+k)\tau}-1}\right)}{\frac{A}{e^{T\alpha}-1}+\frac{B}{e^{T\beta}-1}}$$

$$P_{PTM,\infty,post-dose} = \frac{\left[A\left(\frac{1}{e^{\alpha\tau}-1}-\frac{1-P_0}{e^{(\alpha+k)\tau}-1}\right)+B\left(\frac{1}{e^{\beta\tau}-1}-\frac{1-P_0}{e^{(\beta+k)\tau}-1}\right)\right]+P_0(A+B)}{\frac{Ae^{\alpha\tau}}{e^{\alpha T}-1}+\frac{Be^{\beta T}}{e^{\beta T}-1}}$$

The equation constants A, B, α, β, and k can be solved by fitting the equation to experimental results obtained in the first dosing interval.

In various embodiments, the post-translational modification comprises a product quality attribute that can potentially impact drug stability, safety, and/or efficacy. In certain embodiments, the method is used to monitor the in vivo post-translational modification profile of a monoclonal antibody, such as a recombinant therapeutic monoclonal antibody. In some cases, the method further includes creating a predictive model of the in vivo progression of post-translational modifications and a subject's exposure to product quality attributes. In some embodiments, the post-translational modification comprises one or more of deamidation, oxidation, glycation, disulfide formation, N-terminal pyroglutamate formation, C-terminal lysine removal, and/or high mannose glycosylation. In some embodiments, the method further includes modeling a correlation between PK concentration and proportion of post-translational modification variants. In some embodiments, the method further includes quantitatively assessing and predicting a subject's exposure to a representative post-translational modification in both single- and multiple-dose regimens. In some embodiments, the method further includes predicting the maximum and minimum post-translational modification levels observed in the multiple-dose regimens.

Exemplary Computer System

Figure 12:
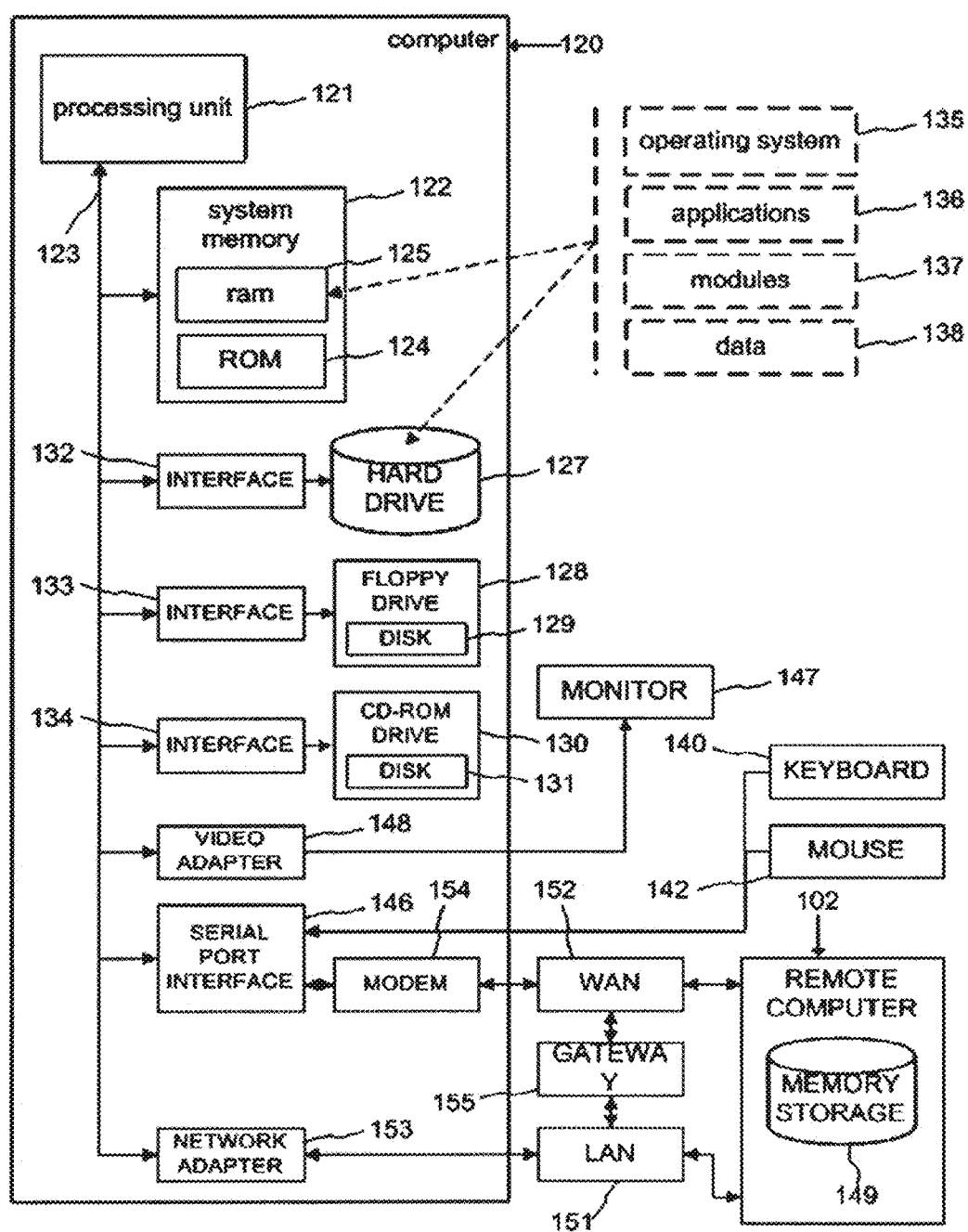
FIG. 12 is a block diagram of a computer system that can be used to implement aspects of the present disclosure.

With reference to FIG. 12 an exemplary computer system for implementing the disclosed method includes a computer 120 (such as a personal computer, laptop, palmtop, set-top, server, mainframe, hand held device, and other varieties of computer), including a processing unit 121, a system memory 122, and a system bus 123 that couples various system components including the system memory to the processing unit 121. The processing unit can be any of various commercially available processors, including INTEL® x86, PENTIUM® and compatible microprocessors from INTEL® and others, including Cyrix, AMD and Nexgen; Alpha from Digital; MIPS from MIPS Technology, NEC, IDT®, Siemens, and others; and the PowerPC from IBM® and Motorola. Dual microprocessors and other multi-processor architectures also can be used as the processing unit 121.

The system bus can be any of several types of bus structure including a memory bus or memory controller, a peripheral bus, and a local bus using any of a variety of conventional bus architectures such as PCI, VESA, AGP, MicroChannel, ISA and EISA, to name a few. A basic input/output system (BIOS), containing the basic routines that help to transfer information between elements within the computer 120, such as during start-up, is stored in ROM 124. The system memory includes read only memory (ROM) 124 and random access memory (RAM) 125. The computer 120 may further include a hard disk drive 127, a magnetic disk drive 128, for example to read from or write to a removable disk 129, and an optical disk drive 130, for example to read a CD-ROM disk 131 or to read from or write to other optical media. The hard disk drive 127, magnetic disk drive 128, and optical disk drive 130 are connected to the system bus 123 by a hard disk drive interface 132, a magnetic disk drive interface 133, and an optical drive interface 134, respectively. The drives and their associated computer readable media provide nonvolatile storage of data, data structures (databases), computer executable instructions, etc. for the computer 120. Although the description of computer readable media above refers to a hard disk, a removable magnetic disk and a CD, it should be appreciated by those skilled in the art that other types of media which are readable by a computer, such as magnetic cassettes, flash memory cards, digital video disks, Bernoulli cartridges, and the like, can also be used in the exemplary operating environment.

Data can be stored in the drives and RAM 125, including an operating system 135, one or more application programs 136, other program modules 137, and program data 138. A user can enter commands and information into the computer 120 using various input devices, such as a keyboard 140 and pointing device, such as a mouse 142. Other input devices (not shown) can include a microphone, satellite dish, scanner, or the like. These and other input devices are often connected to the processing unit 121 through a serial port interface 146 that is coupled to the system bus, but can be connected by other interfaces, such as a parallel port, game port or a universal serial bus (USB). A monitor 147 or other type of display device is also connected to the system bus 123 via an interface, such as a video adapter 148. In addition to the monitor, computers typically include other peripheral output devices (not shown), such as printers. Alternatively, the display medium is a print-out or other tangible medium. The output information can also be preserved in a computer readable medium for storage and/or subsequent use or display.

The computer 120 can operate in a networked environment using logical connections to one or more other computer systems, such as computer 102. The other computer systems can be servers, routers, peer devices or other common network nodes, and typically include many or all of the elements described relative to the computer 120, although only a memory storage device 149 has been illustrated in FIG. 12. The logical connections depicted in FIG. 12 include a local area network (LAN) 151 and a wide area network (WAN) 152. Such networking environments are common in offices, enterprise-wide computer networks, intranets and the Internet.

When used in a LAN networking environment, the computer 120 is connected to the local network 151 through a network interface or adapter 153. When used in a WAN networking environment, the computer 120 typically includes a modem 154 or other means for establishing communications (for example via the LAN 151 and a gateway or proxy server 155) over the wide area network 152, such as the Internet. The modem 154, which can be internal or external, is connected to the system bus 123 via the serial port interface 146. In a networked environment, program modules depicted relative to the computer 120, or portions thereof, can be stored in the remote memory storage device. It will be appreciated that the network connections shown are exemplary and other means of establishing a communications link between the computer systems (including an Ethernet card, ISDN terminal adapter, ADSL modem, IOBaseT adapter, 100BaseT adapter, ATM adapter, or the like) can be used.

The methods, including the acts and operations they comprise, described above can be performed by the computer 120 or by an instrument or other device that is specifically programmed or dedicated to perform the disclosed methods. Hence, the methods can be carried out on a specific machine, such as a device other than a general purpose computer. Such acts and operations are sometimes referred to as being computer executed. It will be appreciated that the acts and symbolically represented operations include the manipulation by the processing unit 121 of electrical signals representing data bits which causes a resulting transformation or reduction of the electrical signal representation, and the maintenance of data bits at memory locations in the memory system (including the system memory 122, hard drive 127, floppy disks 129, and CD-ROM 131) to thereby reconfigure or otherwise alter the computer system's operation, as well as other processing of signals. The memory locations where data bits are maintained are physical locations that have particular electrical, magnetic, or optical properties corresponding to the data bits.

Exemplary Distributed Computing Environment

Figure 13:
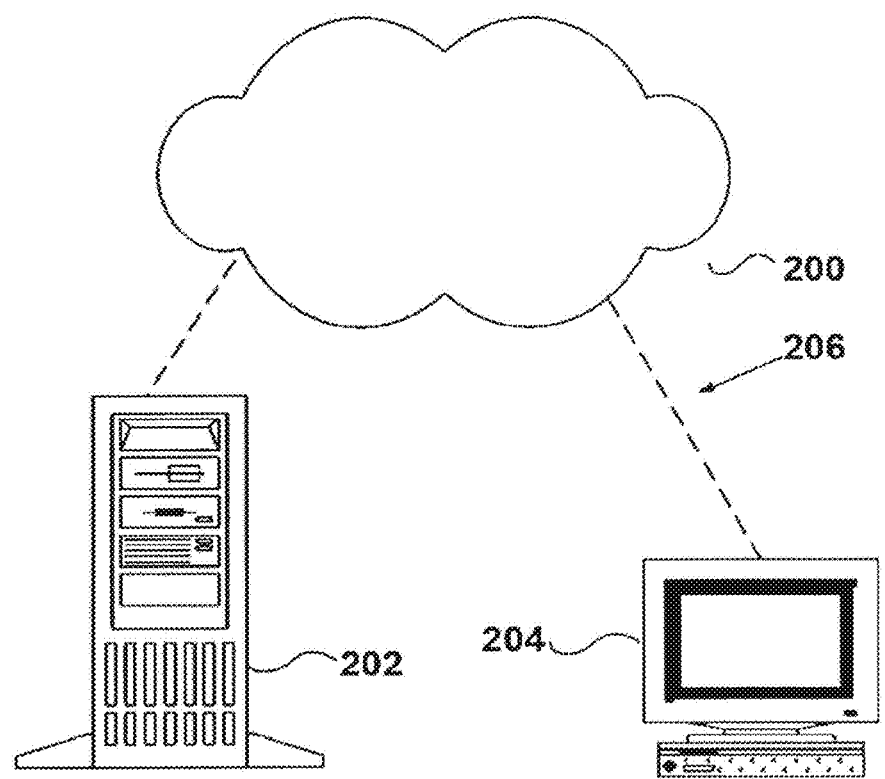
FIG. 13 is a diagram of a distributed computing environment in which aspects of the present disclosure can be implemented.

FIG. 13 illustrates a distributed computing environment in which the software and/or database elements used to implement the methods of the present disclosure may reside. The distributed computing environment 200 includes two computer systems 202, 204 connected by a connection medium 206, although the disclosed method is equally applicable to an arbitrary, larger number of computer systems connected by the connection medium 206. The computer systems 202, 204 can be any of several types of computer system configurations, including personal computers, multiprocessor systems, handheld devices, and the like. In terms of logical relation with other computer systems, a computer system can be a client, a server, a router, a peer device, or other common network node. Additional computer systems 202 or 204 may be connected by an arbitrary number of connection mediums 206. The connection medium 206 can comprise any local area network (LAN), wide area network (WAN), or other computer network, including but not limited to Ethernets, enterprise-wide computer networks, intranets and the Internet.

Portions of the software and databases for storing data can be implemented in a single computer system 202 or 204, with the application later distributed to other computer systems 202, 204 in the distributed computing environment 200. Portions of the software may also be practiced in a distributed computing environment 200 where tasks are performed by a single computer system 202 or 204 acting as a remote processing device that is accessed through a communications network, with the distributed application later distributed to other computer systems in the distributed computing environment 200. In a networked environment, program modules and databases for storing data can be located on more than one computer system 202 or 204. Communication between the computer systems in the distributed computing network may advantageously include encryption of the communicated data.

EXAMPLE

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1

Quantitation and Modeling of Product Quality Attributes of a Therapeutic Monoclonal Antibody in Single- and Multiple-Dose Monkey Pharmacokinetic Studies This example describes the investigation of the number of PQAs of a therapeutic monoclonal antibody, MAB1, using monkey serum samples from single- and multiple-dose PK studies. With affinity purification followed by LC-MS/MS, a number of PTM attributes of MAB1 were assessed, including deamidation, oxidation, N-terminal pyroglutamate, C-terminal lysine removal, and high mannose glycosylation. In addition, models were built to simulate the in vivo progression of PTMs and subject's exposure to PQAs, which provides a quantitative approach to assess the criticality of the PQAs. Asparagine deamidation was used as a representative PTM attribute to evaluate the models. The subject's exposure to deamidated MAB1 simulated by the disclosed models was in good agreement with experimental results for both single- and multiple-dose studies.

Materials and Methods

Materials

The human IgG4 monoclonal antibody (MAB1) and anti-human antibody used in this study were produced at Regeneron Pharmaceuticals, Inc. (Tarrytown, N.Y.). The mean half-life of MAB was approximately 11.5 days. Unless otherwise indicated, all reagents were obtained from Sigma-Aldrich (St. Louis, Mo.) or Thermo Fisher Scientific (Waltham, Mass.).

Preclinical Sample Information

The preclinical serum samples were obtained from either single-dose or multiple-dose cynomolgus monkey PK studies. MAB1 was administered to subjects intravenously (IV). For the single-dose study, animals were dosed at 10 mg/kg, and serum samples were collected at designated time points (pre-dose, 5-minute, 4-hour, 12-hour, 1-day, 3-day, 7-day, 14-day, 18-day, 30-day, 42-day, and 56-day) over the course of 8 weeks (56 days). For the multiple-dose study, animals were dosed at 3 mg/kg every 2 weeks (14 days), and serum samples were collected at designated time points (pre-dose, 1-hour, 4-hour, 1-day, 3-day, 7-day) within the first dosing interval as well as before and after each new dose (14-day, 28-day, 42-day, 56-day) over the course of 8 weeks (56 days). The serum samples were stored at −80° C. until analyses. The MAB1 serum concentration at each collected time-point was measured using an enzyme-linked immunosorbent assay (ELISA). In brief, the MAB1 was captured on a microtiter plate coated with drug target. The MAB1 captured on the plate was detected using biotinylated mouse anti-human IgG4 monoclonal antibody, followed by NeutrAvidin conjugated to horseradish peroxidase (NeutraAvidin-HRP). A luminol-based substrate specific for peroxidase was then added to achieve a signal intensity that is proportional to the concentration of MAB1.

Affinity Purification of MAB1 from Serum Samples

MAB1 was purified from the collected monkey serum samples by affinity purification. In brief, biotinylated anti-human antibody was conjugated to Dynabeads MyOne Streptavidin T1 magnetic beads (Invitrogen, Carlsbad, Calif.) at room temperature for 10 minutes. The conjugated beads were incubated with serum samples at room temperature for 30 minutes. The beads were washed with HBS-EP buffer (GE Healthcare, Pittsburgh, Pa.), and then eluted with 0.1% formic acid and 50% acetonitrile. A bioanalyzer (Agilent Technologies, Santa Clara, Calif.) was used to assess the recovery rate of MAB1 during the affinity purification. A known amount of 230 kDa high molecular-weight standard from Agilent (shown as "Upper Marker") was run with each sample as an internal normalization control. The ratio of the MAB1 peak area to the Upper Marker peak area in each sample was calculated to correct for run-to-run variability. The recovery rate of MAB1 during the affinity purification was calculated using the following equation:

$$\text{Recovery Rate} = \frac{\text{Peak Area Ratio of } MAB1 \text{ to Upper Marker in "Eluate"}}{\text{Peak Area Ratio of } MAB1 \text{ to Upper Marker in "}MAB1 \text{ Input"}} \times 100\%$$

Equation 1

Tryptic Digestion

The purified MAB1 samples were dried down using a vacuum concentrator (LABCONCO, Kansas City, Mo.). The dried samples were re-suspended in 8M urea and 10 mM TCEP, and incubated at 37° C. for 30 minutes. The reduced cysteine residues were alkylated with 10 mM of iodoacetamide at room temperature for 30 minutes in the dark. Following alkylation, the urea concentration was diluted to 1.25M prior to digestion. Trypsin (Promega, Sunnyvale, Calif.) was added was added to the samples at an enzyme:substrate ratio of 1:10 and incubated at 37° C. for 4 hours. Digestion was terminated by addition of 20% formic acid (FA; Thermo Scientific, San Jose, Calif.). The digested samples were stored at −80° C. until analysis.

LC-MS/MS and Data Analysis

Peptides generated by trypsin digestion were separated using an Acquity UPLC CSH C18 1.7 μm, 2.1 mm×150 mm column (Waters, Milford, Mass.) on an Acquity I-Class UPLC system (Waters, Milford, Mass.) coupled to a Q Exactive plus mass spectrometer (Thermo Fisher Scientific, San Jose, Calif.). The mobile phase A was 0.1% of FA in water and mobile phase B was 0.1% FA in acetonitrile. A gradient from 2% mobile phase B to 30% mobile phase B for 56 min at a flow rate of 0.25 mL/min was used for peptide separation. The MS acquisition consisted of a full mass scan followed by tandem mass (MS/MS) scans of the top 5 highest intensity ions of each full scan. Peptide and PTM identification were determined by Byonic (version 2.16.11, Protein Metrics Inc., San Carlos, Calif.) and verified manually. To quantify relative abundance of PTMs, the extracted ion chromatograms, based on the m/z of the first isotope peak of both the modified peptide and native peptide, were generated and the extracted peak areas were integrated using Skyline-daily (version 4.1.1.18151) using a mass window of 5 ppm. The percentage of each PTM variant was calculated using the extracted ion chromatogram (EIC) peak area of the modified peptide relative to the sum of the peak areas of the modified and native peptides.

Calculation of the subject's exposure to a quality attribute in the single-dose PK study Quantitative assessment of the subject's exposure to a quality attribute in a single-dose PK study was described previously by Flynn et al. (Goetze et al., mAbs 2010; 2:500-7). The MAB1 serum concentration-time equation can be described by a two-compartment model (Rowland and Tozer Wolters Kluwer Health/Lippincott William & Wilkins, 2011):

$$C(t) = \text{Dose} \times (C_1 e^{-\lambda_1 t} + C_2 e^{-\lambda_2 t})$$

Equation 2, where C(t) is the serum concentration of MAB1; $C_1$, $C_2$, $\lambda_1$, and $\lambda_1$ are hybrid constants.

To simplify for the readability, the below format was adopted:

$$C(t) = Ae^{-\alpha t} + Be^{-\beta t}$$

Equation 3, where A and B are the zero-time intercepts (hybrid coefficients); α and β are the hybrid first-order constants, respectively. The equation was fitted to the ELISA-measured MAB1 serum concentrations at the collected time points to find the best-fit parameters. The fitting constrains were: C(0) must be greater than the first post-dose ELISA-measured MAB1 serum concentration; C (infinite) constant equal to 0; A and B must be greater than 0. R square was used to quantify goodness-of-fit and a R square greater than 0.95 was considered as a good fit.

The relative abundance of MAB1 with deamidation at a site-specific Asn can be described by a first-order kinetic equation:

$$P_{deam}(t) = 1 - (1 - P_0) \cdot e^{-k_{deam} t}$$

Equation 4, where $P_{deam}(t)$ is the percentage of the deamidation; $P_0$ is the initial deamidation level on Day 0; $k_{deam}$ is the deamidation rate constant.

The serum concentration of MAB1 with deamidation at a specific Asn site can be described as:

$$C_{deam}(t) = C(t) \cdot P_{deam}(t)$$

Equation 5, where $C_{deam}(t)$ is the serum concentration of MAB1 with deamidation at a specific Asn site. The area under the curve (AUC) of $C_{deam}(t)$ represents the subject's exposure to the quality attribute (i.e., MAB1 with deamidation at a specific Asn site. Equations describing C(t) and $P_{deam}(t)$ were solved by nonlinear regression using JMP (version 13.2.1, SAS, Cary, N.C.). $C_{deam}(t)$ was calculated using Excel (Microsoft, Redmond, Wash.) and plotted using JMP. The subject's exposure, represented by AUC of $C_{deam}(t)$, was calculated using JMP.

Calculation of the Subject's Exposure to a Quality Attribute in the Multiple-Dose PK Study Modeling the subject's exposure to a quality attribute in the multiple-dose PK study was mathematically simplified using the superposition principle as the linear accumulation of multiple single-doses. The serum concentration of MAB1 following each dose was described by a two-compartment model, discussed in the single-dose PK study above. The serum concentration of MAB1 immediately before the $m^{th}$ dose can be described as follows:

$$C_{m,pre-dose}(m \cdot \tau) = C[(m-1) \cdot \tau] + \ldots + C(1 \cdot \tau)$$

Equation 6, where m is the number of doses and τ is the time interval between doses.

The serum concentration of MAB1 immediately after the $m^{th}$ dose can be described as follows:

$$C_{m,post-dose}(m \cdot \tau) = C[(m-1) \cdot \tau] + \ldots + C(1 \cdot \tau) + C(0) \quad \text{Equation 7}$$

When m approaches infinity, the $C_{m,pre-dose}$ and $C_{m,after-dose}$ approach the steady-state concentrations, described as follows:

$$C_{\infty,steady-state,pre-dose} = \quad \text{Equation 8}$$

$$\sum_{i=1}^{\infty}(A \cdot e^{-\alpha\tau i} + B \cdot e^{-\beta\tau i}) = \frac{A}{e^{\alpha\tau} - 1} + \frac{B}{e^{\beta\tau} - 1}$$

$$C_{\infty,steady-state,post-dose} = \quad \text{Equation 9}$$

$$\sum_{i=0}^{\infty}(A \cdot e^{-\alpha\tau i} + B \cdot e^{-\beta\tau i}) = \frac{Ae^{\alpha\tau}}{e^{\alpha\tau} - 1} + \frac{Be^{\beta\tau}}{e^{\beta\tau} - 1}$$

The serum concentration of MAB1 with deamidation at a specific Asn site immediately before the $m^{th}$ dose can be described as follows:

$$C_{deam,m,pre-dose}(m \cdot \tau) = P_{deam}[(m-1) \cdot \tau]$$
$$C[(m-1) \cdot \tau] + \ldots + P_{deam}(1 \cdot \tau)C(1 \cdot \tau) \quad \text{Equation 10}$$

The serum concentration of MAB1 with deamidation at a specific Asn site determined immediately following the $m^{th}$ dose can be described as follows:

$$C_{deam,m,post-dose}(m \cdot \tau) = P_{deam}[(m-1) \cdot \tau]$$
$$C[(m-1) \cdot \tau] + \ldots + P_{deam}(1 \cdot \tau)C(1 \cdot \tau) +$$
$$P_{deam}(0)C(0) \quad \text{Equation 11,}$$

where $P_{deam}(t)$ is the first-order reaction equation, discussed in the single-dose PK study above.

Thus, the relative abundance of MAB1 with deamidation at a specific Asn site immediately before the $m^{th}$ dose can be described as follows:

$$P_{deam,m,pre-dose}(m \cdot \tau) = \frac{C_{deam,m,pre-dose}(m \cdot \tau)}{C_{m,pre-dose}(m \cdot \tau)} \quad \text{Equation 12}$$

The relative abundance of MAB1 with deamidation at a specific Asn site immediately following the $m^{th}$ dose can be described as follows:

$$P_{deam,m,post-dose}(m \cdot \tau) = \frac{C_{deam,m,post-dose}(m \cdot \tau)}{C_{m,post-dose}(m \cdot \tau)} \quad \text{Equation 13}$$

When m approaches infinity, the $P_{deam,m,pre-dose}$ and $P_{deam,m,after-dose}$ approach the steady-state levels, described as follows:

$$P_{deam,\infty,steady-state,pre-dose} = \frac{1}{C_{\infty,pre-dose}} \sum_{i=1}^{\infty} P_{deam}(i) \cdot C(i) = \quad \text{Equation 14}$$

$$\frac{1}{C_{\infty,pre-dose}} \sum_{i=1}^{\infty} [1 - (1 - P_0)e^{-k\tau i}](A \cdot e^{-\alpha\tau i} + B \cdot e^{-\beta\tau i})$$

$$P_{deam,\infty,steady-state,post-dose} = \quad \text{Equation 15}$$

$$\frac{P_{deam,\infty,pre-dose} \cdot C_{\infty,pre-dose} + P_{deam}(0) \cdot C(0)}{C_{\infty,post-dose}}$$

Since the calculation of the summation terms converges, the pre-dose levels of deamidation at the steady state can be simplified as follows:

$$P_{deam,\infty,steady-state,pre-dose} = \frac{A\left(\frac{1}{e^{\alpha\tau} - 1} - \frac{1 - P_0}{e^{(\alpha+k)\tau} - 1}\right) + B\left(\frac{1}{e^{\alpha\tau} - 1} - \frac{1 - P_0}{e^{(\beta+k)\tau} - 1}\right)}{\frac{A}{e^{T\alpha} - 1} + \frac{B}{e^{T\beta-1}}} \quad \text{Equation 16}$$

Therefore, the post-dose level of deamidation at the steady state can be simplified as follows:

$$P_{deam,\infty,steady-state,post-dose} = \quad \text{Equation 17}$$

$$\frac{\left[A\left(\frac{1}{e^{\alpha\tau} - 1} - \frac{1 - P_0}{e^{(\alpha+k)\tau} - 1}\right) + B\left(\frac{1}{e^{\beta\tau} - 1} - \frac{1 - P_0}{e^{(\beta+k)\tau} - 1}\right)\right] + P_0(A + B)}{\frac{Ae^{\alpha\tau}}{e^{\alpha\tau} - 1} + \frac{Be^{\beta\tau}}{e^{\beta\tau} - 1}}$$

The equation constants A, B, α, β, and k were solved by fitting the equation to the experimental results within the first dosing interval. The simulated and predicted values were calculated using Excel and then plotted using JMP. The subject's exposure (i.e., AUC) was calculated using JMP.

Results

Quantitation of Post-Translational Modifications of MAB1 In Vivo

The in vivo dynamics of MAB1 variants with various PTMs were assessed in both single- and multiple-dose monkey PK studies.

A biotinylated anti-human Fc antibody conjugated on streptavidin magnetic beads was used to extract MAB1 from the monkey serum samples. The affinity purification recovery rate of MAB1 was >99.5% (FIG. 1), which demonstrated that the affinity purification approach can completely extract both native MAB1 and its PTM variants, ensuring accurate quantitation of the relative PTM abundance of each PTM.

Figure 2B:
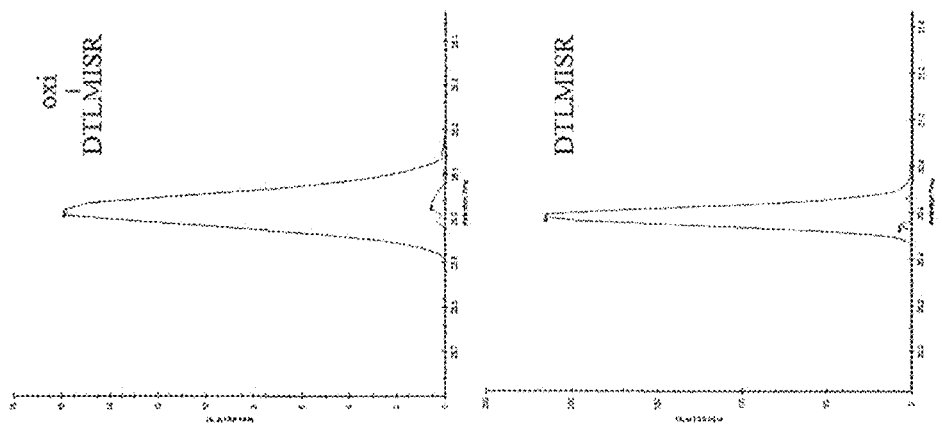
FIGS. 2A and 2B are example MS/MS spectra of peptide identification (FIG. 2A) and example extracted ion chromatograms for peptide peak integration and PTM quantitation (FIG. 2B).
Figure 2A:
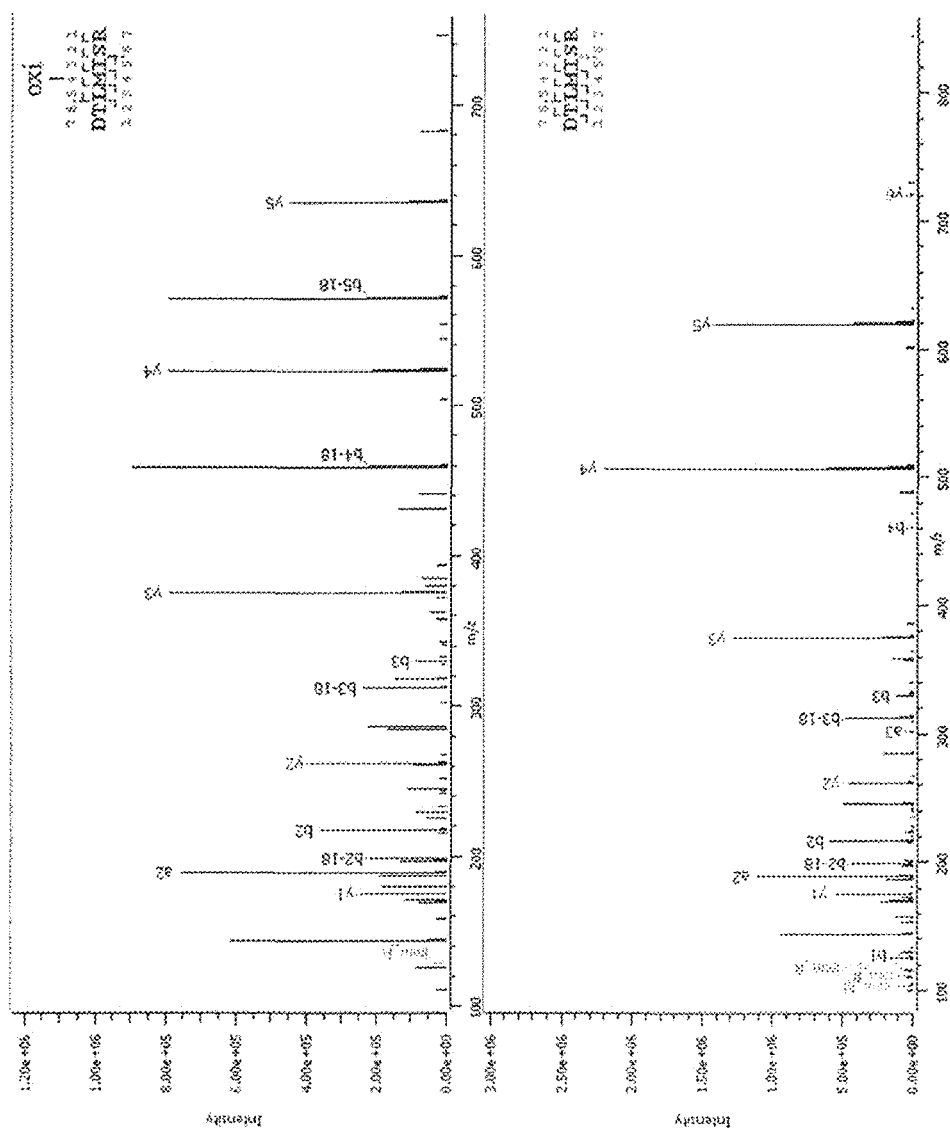

FIG. 2A shows example tandem MS spectra of the identification of a wildtype Fc tryptic peptide "DTLMISR" (SEQ ID NO: 1)(bottom panel) and the corresponding methionine (Met) oxidized peptide (upper panel). FIG. 2B shows the extracted ion chromatograph peak areas of the wildtype peptide (bottom panel) and the corresponding Met oxidized peptide (upper panel).

Figure 3A:
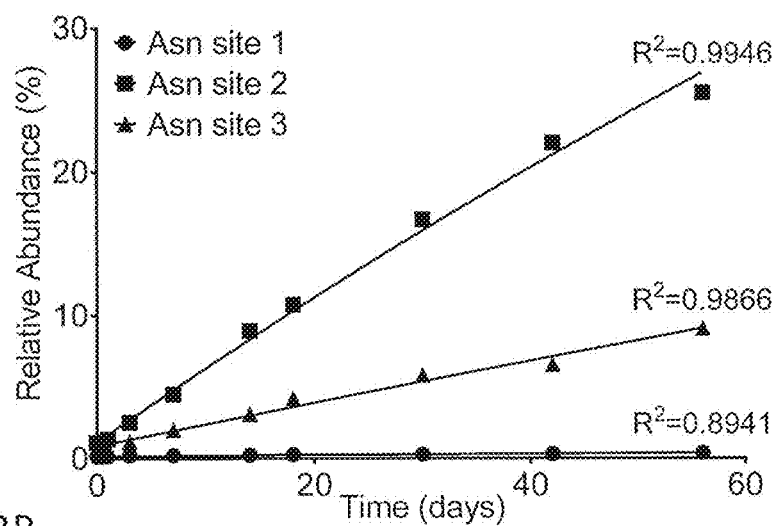
FIGS. 3A and 3B are graphs showing the relative abundance of deamidation at each of the three Asn sites in the Fc region of MAB1 from the single-dose PK study (FIG. 3A) and the multiple-dose PK study (FIG. 3B).

Deamidation of asparagine (Asn) is a common PTM in the highly conserved fragment crystallizable (Fc) region of mAbs (Chelius et al., Analytical Chemistry 2005; 77:6004-11; Sinha et al., Protein Science: a publication of the Protein Society 2009; 18:1573-84). Three common deamidation sites, "NG" (Asn Site 1) in CH2 domain, "NG" (Asn Site 2) and "NN" (Asn Site 3) in the PENNY peptide of the CH3 domain were monitored in this study. In this work, three deamidation sites of Asn, "NG" (Asn site 1) in the CH2 domain, "NG" (Asn site 2) and "NN" (Asn site 3) in the CH3 domain were monitored. In the single-dose PK study, the relative abundance of deamidation at Asn site 1 remained nearly unchanged at a low level of ~0.2% over 56 days (FIG. 3A). The relative abundance of deamidation of Asn Site 2 and Asn Site 3 increased from ~1% to 25.5% and 9.1% over 56 days, respectively (FIG. 3A). The deamidation rate depends on the primary amino acid sequence, protein structure, pH, temperature, and buffer composition (Chelius et al., Analytical Chemistry 2005; 77:6004-11; Sinha et al., Protein Science: a publication of the Protein Society 2009; 18:1573-84; Kossiakoff, Science 1988; 240:191-4; Athmer et al., The Journal of Biological Chemistry 2002; 277:30502-7; Xie et al., Journal of Pharmaceutical Sciences 1999; 88:8-13; Wearne et al., Proteins 1989; 5:8-12; Capasso et al., The Journal of Peptide Research: official journal of the American Peptide Society 1999; 54:377-82; Song Y et al., Journal of Pharmaceutical Sciences 2001; 90:141-56; Wakankar et al., Journal of Pharmaceutical Sciences 2006; 95:2321-36; Zheng et al., International Journal of Pharmaceutics 2006; 308:46-51; Pace et al., Journal of Pharmaceutical Sciences 2013; 102:1712-23). An Asn residue followed by glycine (Gly) or Serine (Ser) within the primary amino acid sequence is particularly susceptible to deamidation (Patel et al., Pharmaceutical Research 1990; 7:787-93; Stephenson et al., The Journal of Biological Chemistry 1989; 264:6164-70; et al., Proceedings of the National Academy of Sciences of the United States of America 2001; 98:944-9; Robinson et al., The Journal of Peptide Research: official journal of the American Peptide Society 2004; 63:426-36). The "NG" and "NN" sites are fully exposed to solvent, and therefore more susceptible to deamidation (DeLano et al., Science 2000; 287:1279-83) than the "NG" site in the CH2 domain (DeLano et al., Science 2000; 287:1279-83).

The deamidation rate can be described using the first-order rate equation as previously established (Geiger et al., The Journal of Biological Chemistry 1987; 262:785-94). The rate equation can be expressed as $P_{deam}(t)=1-(1-P_0)\cdot e^{k_{deam}t}$ where $P_{deam}(t)$, as described in the Materials and Methods. is the proportion of the deamidation as a function of time; $P_0$ is the initial deamidation level; $k_{deam}$ is the deamidation rate constant. The equation was non-linearly fitted to the LC-MS measured deamidation levels in the single dose study to determine the best-fit parameters (FIG. 3A and Table 1). The in vivo deamidation rate constants of Asn Site 1, 2, and 3 were non-linearly fitted to be 0.003278% day$^{-1}$, 0.5384% day$^{-1}$, and 0.1566% day$^{-1}$, respectively with a $R^2$ of 0.9946, 0.9866, and 0.8941, respectively (Table 1).

Figure 3B:
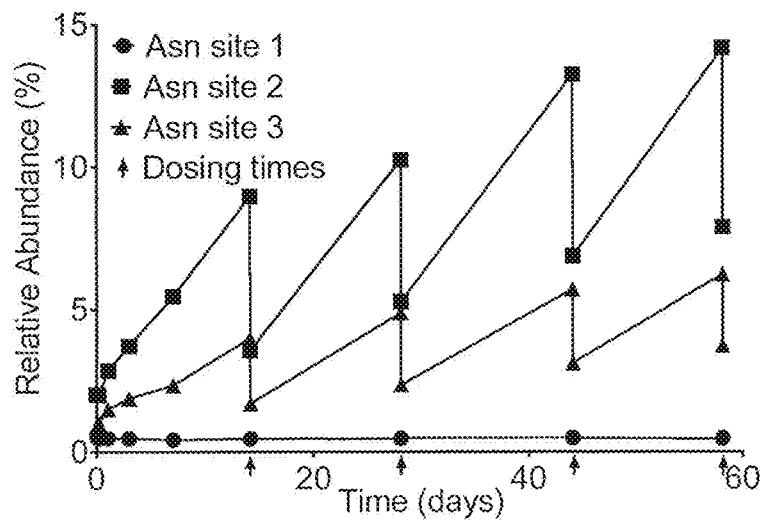
Figure 4A:
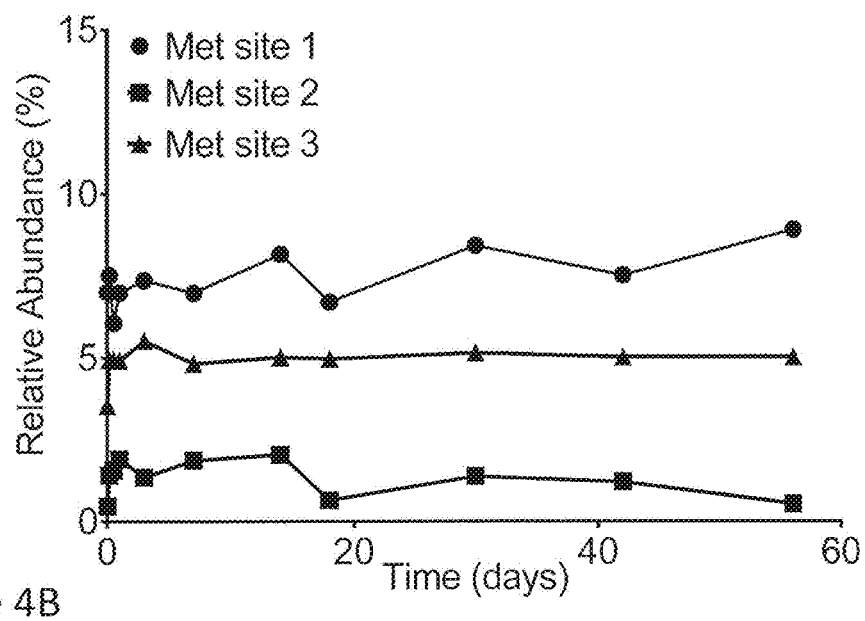
FIGS. 4A and 4B are graphs showing the relative abundance of oxidation at each of the three Met sites in the MAB1 Fc regions from the single-dose PK study (FIG. 4A) and the multiple-dose PK study (FIG. 4B).
Figure 4B:
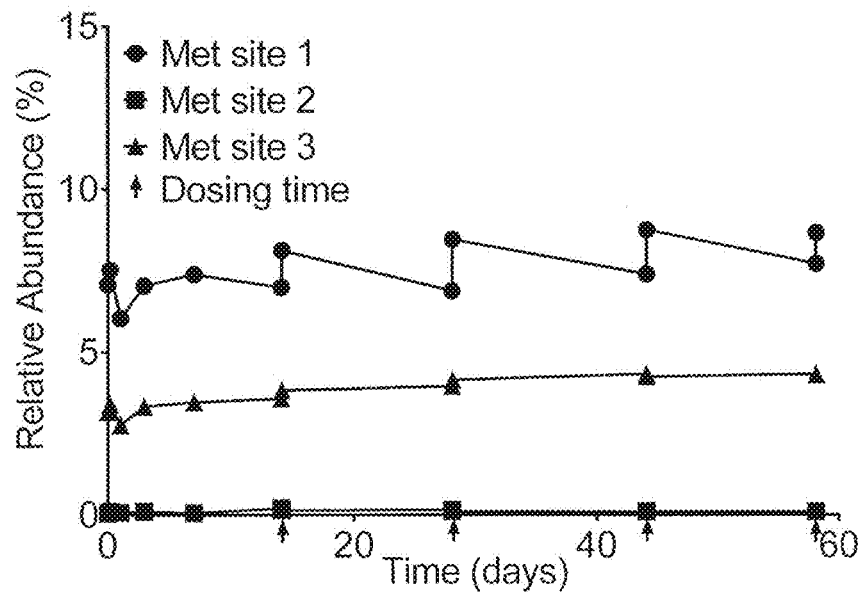

$5^{th}$ dose on Day 56 increased to 14.2% while the post-dose level reached 7.9% (FIG. 3B). The pre-dose level of deamidation at Asn site 3 prior to the $5^{th}$ dose on Day 56 increased to 6.2% while the post-dose level reached 3.6% (FIG. 3B). As a result, the relative abundance of deamidation at Asn site 2 and 3 exhibited a saw-tooth pattern with an increasing trend over time (FIG. 3B). FIG. 3B also suggests that both pre-dose and post-dose levels of deamidation will approach to a steady-state after a finite number of doses. To predict the steady-state levels of deamination, a 2-compartment model for MAB1 concentrations was built that will be discussed in the modeling sections below. Met oxidation is another common PTM in mAbs (Yin et al., Pharmaceutical research 2013; 30:167-78; Li et al., mAbs 2016:0; Li et al., mAbs 2016:0; Liu et al., The Journal of biological chemistry 2011; 286:11211-718). Met oxidation in the Fc region has been shown to impact the Fc receptor binding (Pan et al., Protein Science: a publication of the Protein Society 2009; 18:424-33). In this work, three common Met oxidation sites in the Fc region were evaluated, Met Site 1 in CH2 domain as well as Met Site 2 and 3 in the CH3 domain. In the single-dose study, relative abundance of oxidation at Met Site 1, 2, and 3 were relatively unchanged over 56 days at a level of ~8.0%, ~2.0%, and ~5.0%, respectively (FIG. 4A). In the multiple-dose study, the level of oxidation at Met Site 1 decreased slightly during each dosing interval and increased slightly after each dose, exhibiting a saw-tooth pattern that fluctuates between ~7.0% and ~9.0%. The levels of oxidation at Met site 2 and 3 remained stable at a level of ~1.0% and 4.0%, respectively, in the multiple-dose study (FIG. 4B).

The N-terminal glutamine and glutamate at the N-termini of mAbs are prone to form pyroglutamate through chemical or enzymatic cyclization. The conversion of glutamine occurs much faster than that of glutamate (Yin et al., Pharmaceutical research 2013; 30:167-78; Li et al., mAbs 2016:0; Li et al., mAbs 2016:0; Liu et al., The Journal of biological chemistry 2011; 286:11211-718). The N-terminal cyclized protein is resistant to digestion by amino peptidases, preventing degradation. Although glutaminyl cyclase, an enzyme that catalyzes this conversion, is found in human blood (Schilling et al., Biological Chemistry 2008; 389:983-

TABLE 1

The best-fit parameter values in the modification rate equations from the single-dose PK study

| Deamidation Site | $P_0$ (%) | $k_{deam}$ (day$^{-1}$) | Standard Error of fitted $P_0$ | Standard Error of fitted $k_{deam}$ | $R^2$ |
|---|---|---|---|---|---|
| Asn site 1 | 0.1918 | 0.003523% | 0.00971 | 4.044e−006 | 0.8941 |
| Asn site 2 | 1.143 | 0.5394% | 0.2758 | 0.0001361 | 0.9946 |
| Asn site 3 | 0.8848 | 0.1546% | 0.1389 | 6.09e−005 | 0.9866 |
| N-terminal pyroglutamate | 0.6868 | 0.2201% | 0.1169 | 5.22e−005 | 0.9970 |

Where $P_0$ is the initial deamidation level on Day 0; $k_{deam}$ is the deamidation rate constant.

Figure 5A:
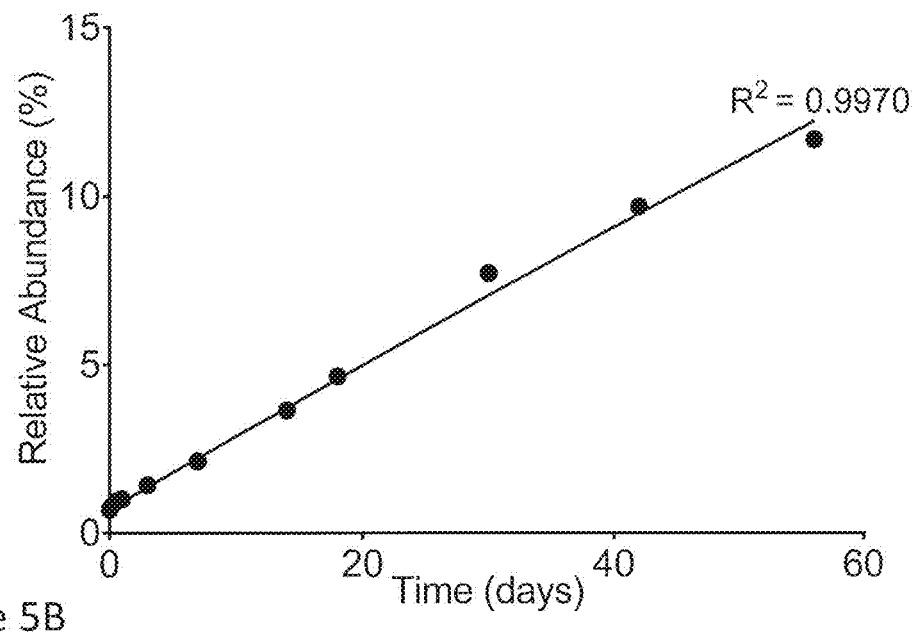
FIGS. 5A and 5B are graphs showing the relative abundances of N-terminal pyroglutamate from the single-dose PK study (FIG. 5A) and the multiple-dose PK study (FIG. 5B).
Figure 5B:
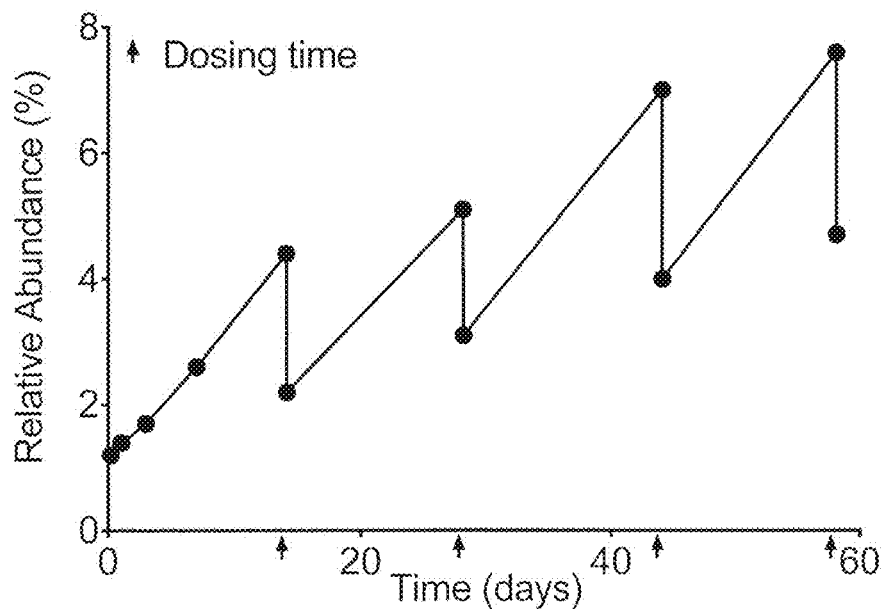

In the multiple-dose study, deamidation of Asn Site 1 remained nearly unchanged at a low level of ~0.5% following 5 biweekly doses over 56 days (FIG. 3B). The relative abundance of deamidation on Asn Sites 2 and 3 accumulated within each dosing interval but dropped sharply after each new dose because of dilution with newly administrated non-deamidated MAB1 (FIG. 3B). The pre-dose and post-dose levels of deamidation gradually increased following each dose due to the accumulation of deamidated MAB1. The pre-dose level of deamidation at Asn site 2 prior to the 91), the formation of pyroglutamate from glutamate of mAbs in vivo is predominantly a pH-dependent non-enzymatic reaction, as it bears the same rate constant in PBS in vitro (Yin et al., Pharmaceutical Research 2013; 30:167-78; Liu et al., The Journal of Biological Chemistry 2011; 286:11211-7). In the single-dose study, N-terminal pyroglutamate increased from 0.7% to 11.7% over 56 days (FIG. 5A). The in vivo N-terminal pyroglutamate formation rate was determined to be 0.2201% day$^{-1}$ with a $R^2$ of 0.9970 using non-linear fitting to the LC-MS measured N-terminal pyroglutamate levels. In the multiple-dose study, N-terminal pyroglutamate formation resembled a saw-tooth pattern similar to Asn deamidation (FIG. 5B). The level of pyroglutamate increased during each dosing interval but reduced sharply after each new dose as a result of dilution with newly administrated unmodified MAB1. Prior to the 5th dose on Day 56, the level of pyroglutamate raised to 7.6% and then dipped to 4.2% following the $5^{th}$ dose (FIG. 5B).

The C-terminal lysine residue of a mAb heavy chain is susceptible to removal by basic carboxypeptidase during protein expression (Dick et al., Biotechnology and Bioengineering 2008; 100:1132-43). Partial removal of the C-terminal lysine leads to charge heterogeneity. The percent of MAB1 drug product containing C-terminal lysine before administration was ~2.0%. In both single and multiple-dose studies, the C-terminal lysine was rapidly removed within one day following each dose (FIG. 6). These observations are consistent with a previously reported study.

Figure 6A:
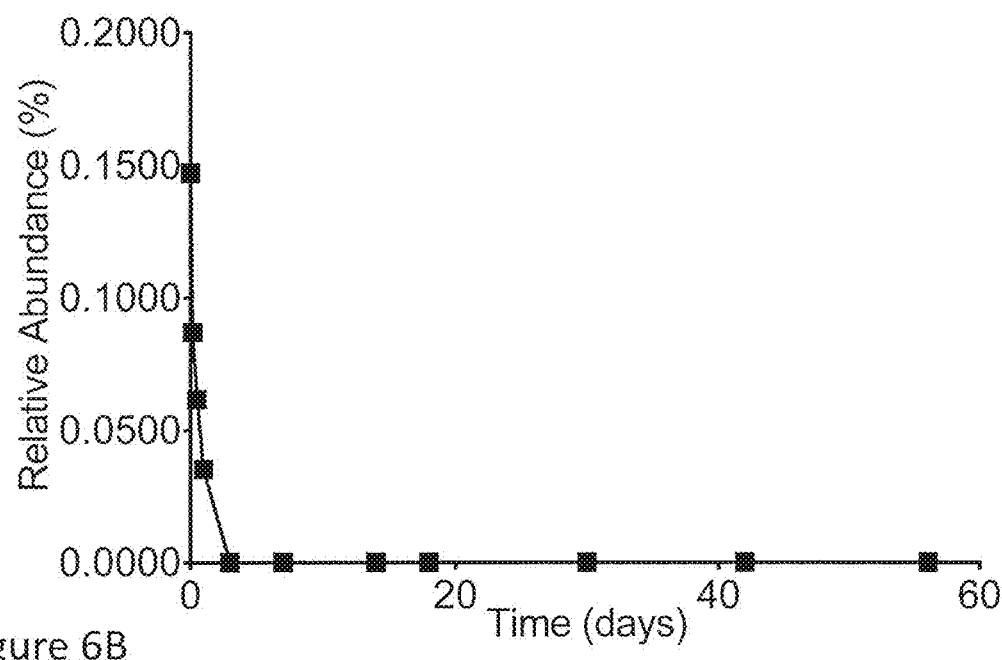
FIGS. 6A and 6B are graphs showing the relative abundances of MAB1 possessing a heavy chain C-terminal lysine from the single-dose PK study (FIG. 6A) and the multiple-dose PK study (FIG. 6B). In both single and multiple-dose studies, the C-terminal lysine was rapidly removed within one day following each dose. Each dosing time is indicated with an arrow "↑".
Figure 6B:
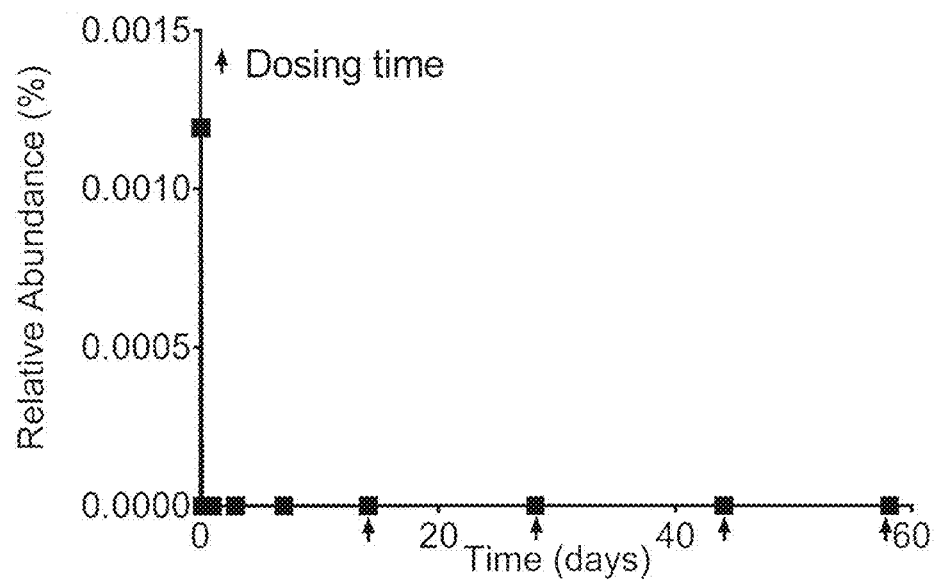

N-linked glycosylation at the Fc region is a commonly monitored PQA of a mAb. The predominant structures of N-linked glycoforms on Chinese Hamster Ovary (CHO) expressed mAbs are typically composed of a core bi-antennary pentasaccharide structure with one or more additional monosaccharides attached. In addition to the complex bi-antennary oligosaccharide structures, high-mannose glycoforms (e.g., Mannose 5) can also be observed on CHO-expressed antibodies. In the single-dose study, the relative abundances of the major glycoforms (fucosylated complex bi-antennary) remained unchanged over 56 days. However, relative abundance of Mannose 5 glycoform decreased from 0.5% to undetectable within 6 weeks (FIG. 6A). This finding is in agreement with faster serum clearance of high-mannose glycoforms due to a high-mannose receptor-mediated clearance pathway (Goetze et al., Glycobiology 2011; 21:949-59; Alessandri et al., mAbs 2012; 4:509-20). In the multiple-dose study, the level of Mannose 5 decreased between during each dosing intervals and evaluated immediately following each new dose because of blending with newly administrated MAB1 with a higher level of Mannose 5, exhibiting a saw-tooth pattern (FIG. 6B). Prior to administration of the $5^{th}$ dose, the level of Mannose 5 decreased to 0.1%. After administration of the $5^{th}$ dose, the level of Mannose 5 increased to 0.4%.

Modeling the Subject's Exposure to the MAB1 PQAs in the Single-Dose Study

Figure 7A:
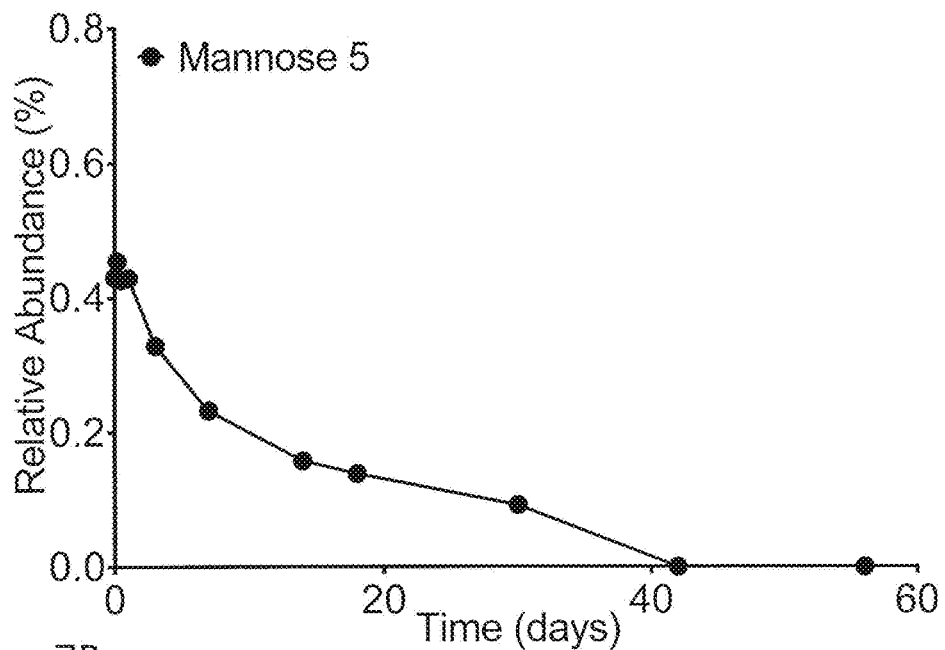
FIGS. 7A and 7B are graphs showing the relative abundances of Mannose 5 glycoform from the single-dose PK study (FIG. 7A) and the multiple-dose PK study (FIG. 7B).
Figure 7B:
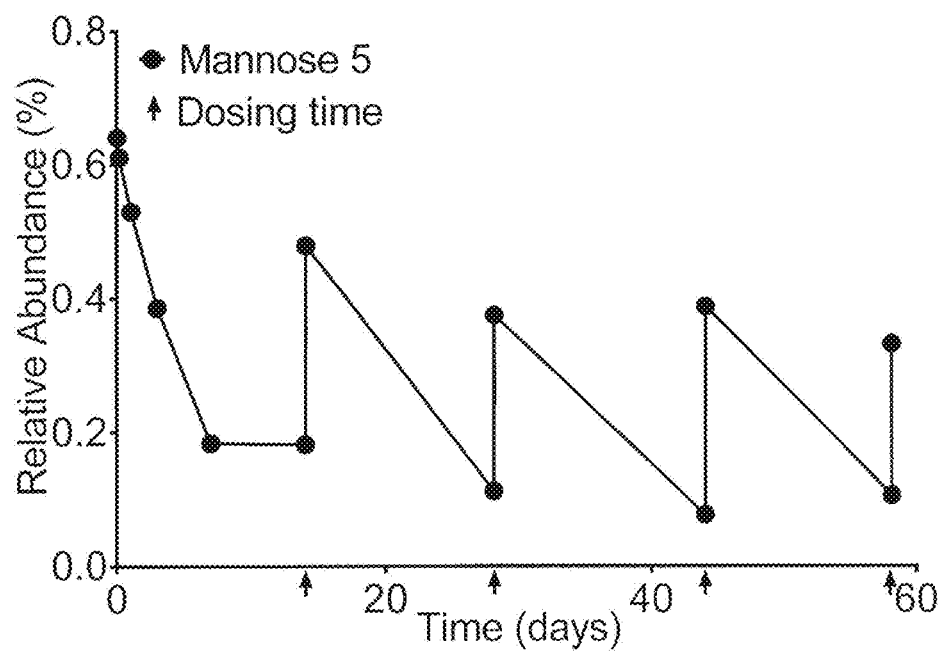

Quantitative assessment of the subject's exposure to mAb quality attributes helps evaluate the impact of quality attributes on drug safety and efficacy. The in vivo serum concentration of a mAb with a certain PTM can be described as $C_{PTM}(t)=C(t) \cdot P(t)$, as described in the Materials and Method section. The area under the curve (AUC) of $C_{PTM}(t)$ corresponds to the subject's exposure to the mAb with the PTM (Goetze et al., mAbs 2010; 2:500-7). In this work, deamidation at Asn site 2 and 3 as well as the N-terminal pyroglutamate formation were used as examples to demonstrate the modeling of the subject's exposure to PQAs in the single-dose study. The modeling was not performed on other PTMs discussed in this paper because Met oxidation was not changed in vivo (FIG. 4); the C-terminal lysine was rapidly removed within hours after administration (FIG. 6); the levels of Mannose 5 and deamidation at Asn site 1 were extremely low (less than 0.5%, FIG. 3 and FIG. 7), making the modeling of these PTMs may not be practically meaningful.

Figure 8A:
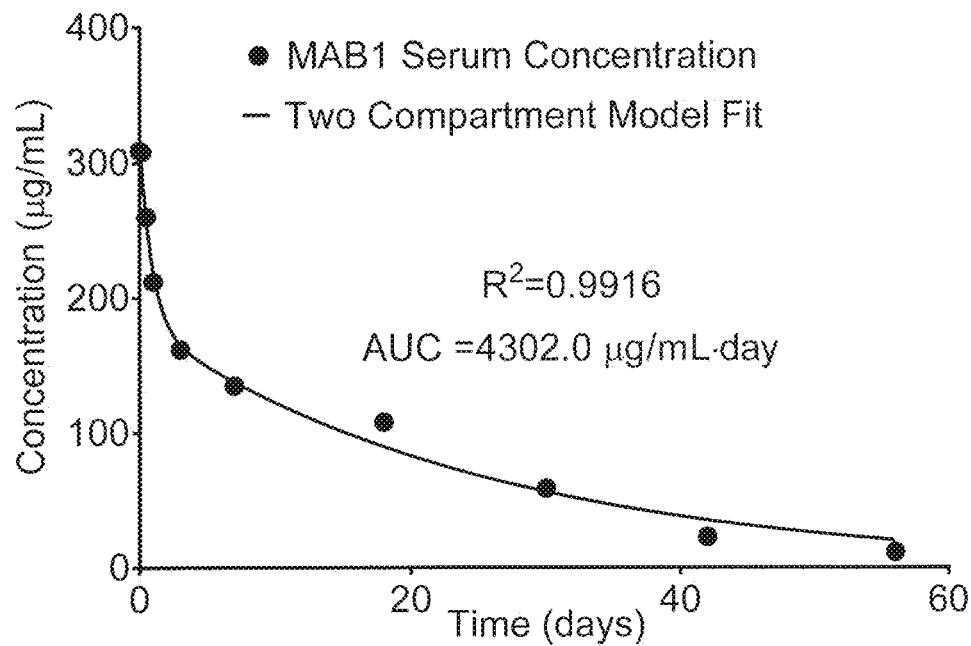
FIG. 8A is graph showing the subject exposure to total MAB1 from the single-dose PK study. The MAB1 serum concentration-time curve (black line) described by the two-compartment pharmacokinetic model equation as $C(t)=Ae^{-\alpha t}+Be^{-\beta t}$ was fitted to the ELISA measured MAB1 serum concentrations (black dots). The subject exposure to total MAB1 over the course of 56 days, represented by the AUC of C(t) was determined as 4302.0 μg/mL·day.

The MAB1 serum concentration-time profile was equation was described by a two-compartment pharmacokinetic model equation as $C(t)=Ae^{-\alpha t}+Be^{-\beta t}$, where A and B are the hybrid coefficients when $\alpha$ and $\beta$ are the hybrid first order constants. The experimental MAB1 serum concentrations from the single-dose PK study were determined using a ELISA assay. The modeling equation was solved by non-linear fitting to the ELISA-measured MAB1 serum concentrations with a $R^2$ of 0.9916 (FIG. 8A). The best-fit values of the parameters in the modeling equation are shown in Table 2. The subject's exposure to the total MAB1 over 56 days, represented by the AUC of C(t), was 4302.0 µg/mL·day (FIG. 8A).

Figure 8B:
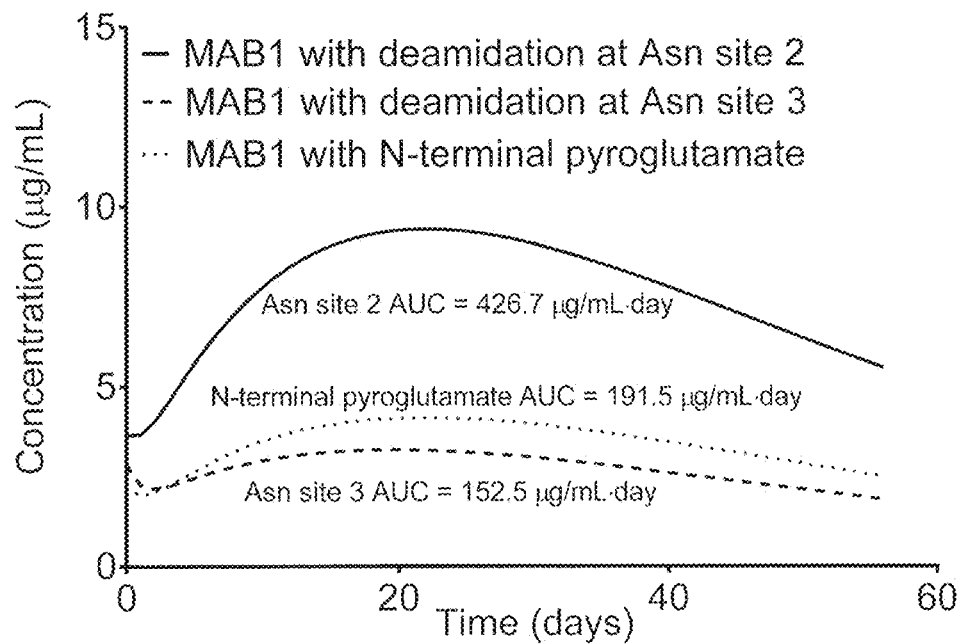
FIG. 8B is a graph showing the subject exposure to MAB1 with a PQA from the single-dose study. The serum concentration-time curve of MAB1 with deamidation is described as $C_{PQA}(t)=C(t)\cdot P_{PQA}(t)$, The AUC of the $C_{PQA}(t)$ curve corresponds to the subject's exposure to MAB1 with the PQA. The subject's exposure to MAB1 with deamidation at Asn site 2 over 56 days was determined as 426.7 μg/mL·day (solid line). The subject's exposure to MAB1 with deamidation at Asn site 3 over 56 days was determined as 152.5 μg/mL·day (dashed line). The subject's exposure to MAB1 with N-terminal pyroglutamate over 56 days was determined as 191.5 μg/mL·day (dot line).

The rate equation of deamidation at Asn site 2 was determined in the previous section above as $P_{deam-Asn2}(t)= 1-(1-0.01143) \cdot e^{-0.005394t}$. The serum concentration-time equation of MAB1 with deamidation at Asn site 2, $C_{deam-Asn2}(t)=C(t) \cdot P_{deam-Asn2}(t)$, can therefore be solved by multiplication of C(t) and $P_{deam-Asn2}(t)$. The curve of $C_{deam-Asn2}(t)$ was plotted in FIG. 8B. The subject's exposure to the MAB1 with deamidation at Asn site 2 over 56 days, represented by the AUC of $C_{deam}(t)$, was calculated to be 426.7 µg/mL·day (FIG. 8B), consisting of 9.9% of the subject's exposure to total MAB1 over 56 days.

Similarly, the rate equation of deamidation at Asn site 3 was determined in the previous section above as $P_{deam-Asn3}(t)=1-(1-0.008848) \cdot e^{-0.001546t}$. The serum concentration-time equation of MAB1 with deamidation at Asn site 3, $C_{deam-Asn3}(t)=C(t) \cdot P_{deam-Asn3}(t)$ can therefore be solved by multiplication of C(t) and $P_{deam-Asn3}(t)$. The curve of $C_{deam-Asn3}(t)$ was plotted in FIG. 8B. The subject's exposure to the MAB1 with deamidation at Asn site 3 over 56 days, represented by the AUC of $C_{deam-Asn3}(t)$, was calculated to be 152.5 µg/mL·day (FIG. 8B), consisting of 3.5% of the subject's exposure to total MAB1 over 56 days.

The rate equation of N-terminal pyroglutamate formation was determined in the previous section above as $P_{PyroE}(t)= 1-(1-0.006868) \cdot e^{-0.002201t}$. The serum concentration-time equation of MAB1 with N-terminal pyroglutmate, $C_{PyroE}(t)= C(t) \cdot P_{PyroE}(t)$, can therefore be solved by multiplication of C(t) and $P_{PyroE}(t)$. The curve of $C_{PyroE}(t)$ was plotted in FIG. 8B. The subject's exposure to the MAB1 with N-terminal pyroglutmate over 56 days, represented by the AUC of $C_{PyroE}(t)$, was 191.5 µg/mL·day (FIG. 8B), consisting of 4.5% of the subject's exposure to total MAB1 over 56 days.

TABLE 2

The best-fit parameters values in the MAB1 serum concentration-time equations from the single-dose PK study and the first dose interval of the multiple-dose PK study

| Study | The single-dose study | The first dose of multiple-dose study |
| --- | --- | --- |
| A | 139.0925 | 57.8676 |
| B | 180.8075 | 25.3133 |
| α | 1.1227 | 0.0413 |
| β | 0.0389 | 0.9286 |
| Standard Error of fitted of A | 15.4245 | 9.9061 |
| Standard Error of fitted of B | 17.3316 | 9.7499 |
| Standard Error of fitted α | 0.3262 | 0.0185 |
| Standard Error of fitted β | 0.0058 | 0.7592 |
| $R^2$ | 0.9916 | 0.9818 |

Modeling the Subject's Exposure to the MAB1 PQAs in the Multiple-Dose Study

Figure 9A:
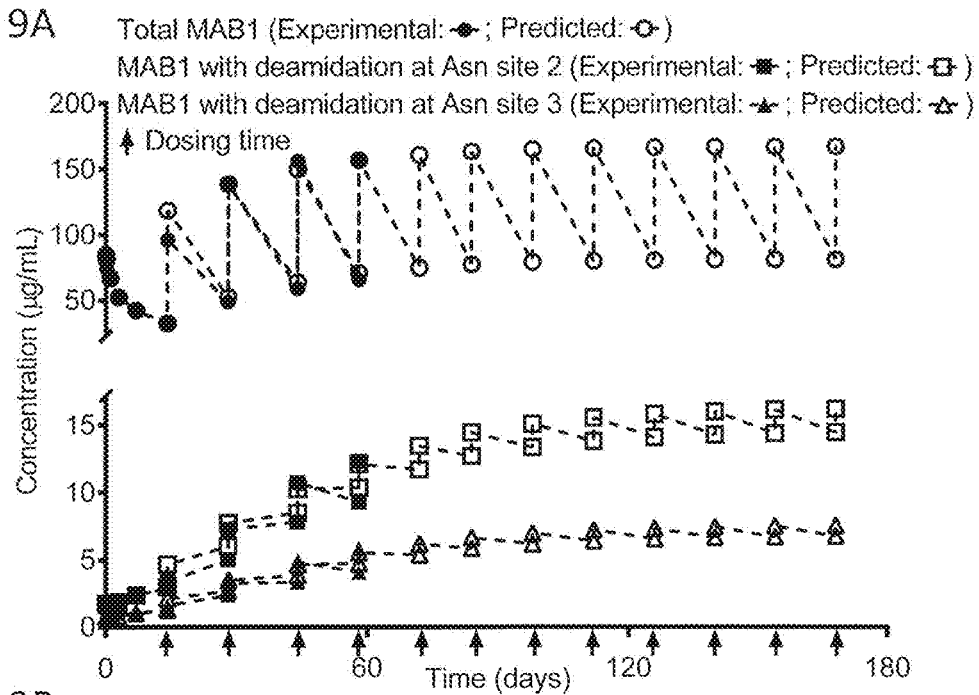
FIG. 9A is a graph showing model predictions and experimental measurements of the serum concentration of total MAB1 and MAB1 with deamidation at Asn site 2 or Asn site 3 from the multiple-dose PK study. The predicted pre-dose and post-dose serum concentrations of total MAB1 and MAB1 with deamidation at Asn site 2 or Asn site 3 are in good agreement with the experimental measurements. The pre-dose and post-dose concentrations of total MAB1 and MAB1 with deamidation at Asn site 2 or 3 approach the steady-state levels following an extended period of dosing.

The subject's exposure to both total MAB1 and MAB1 possessing a specific attribute (e.g. Asn deamidation) can be calculated for any given time interval using the area under the concentration-time curves. The AUCs of the predicted and experimental total MAB1 serum concentration-time curves represent the subject's exposure to total MAB1 over a defined time interval. Based on the predicted and experimental MAB1 serum concentration-time curves (FIG. 9A), the predicted and experimentally determined subject's exposure to total MAB1 over the course of 5 doses (56 days) were 5013 µg/mL·day and 4789 µg/mL·day, respectively. The difference between the predicted and experimental values is 4.7%. Similarly, AUCs of the predicted and experimentally determined concentration-time curves of MAB1 with deamidation at Asn site 2 represent the subject's exposure to MAB1 with deamidation at Asn site 2 over a defined time interval. The predicted and experimentally determined subject's exposure to the Asn site 2-deamidated MAB1 over the course of 5 doses (56 days) were 381.5 µg/mL·day and 352.6 µg/mL·day, respectively (FIG. 9A). The predicted and experimentally determined subject's exposure to the Asn site 2-deamidated MAB1 as a fraction of the subject's exposure to total MAB1 over 56 days were 7.0% and 7.9%, respectively, demonstrating that the models can accurately predict the experimental results.

The predicted and experimentally determined subject's exposure to the Asn site 3-deamidated MAB1 over the course of 5 doses (56 days) were 172.8 µg/mL·day and 158.8 µg/mL·day, respectively (FIG. 9A). The predicted and experimentally determined subject's exposure to the Asn site 3-deamidated MAB1 as a fraction of the subject's exposure to total MAB1 over the span of 56 days were 3.4% and 3.3%, respectively.

Figure 10A:
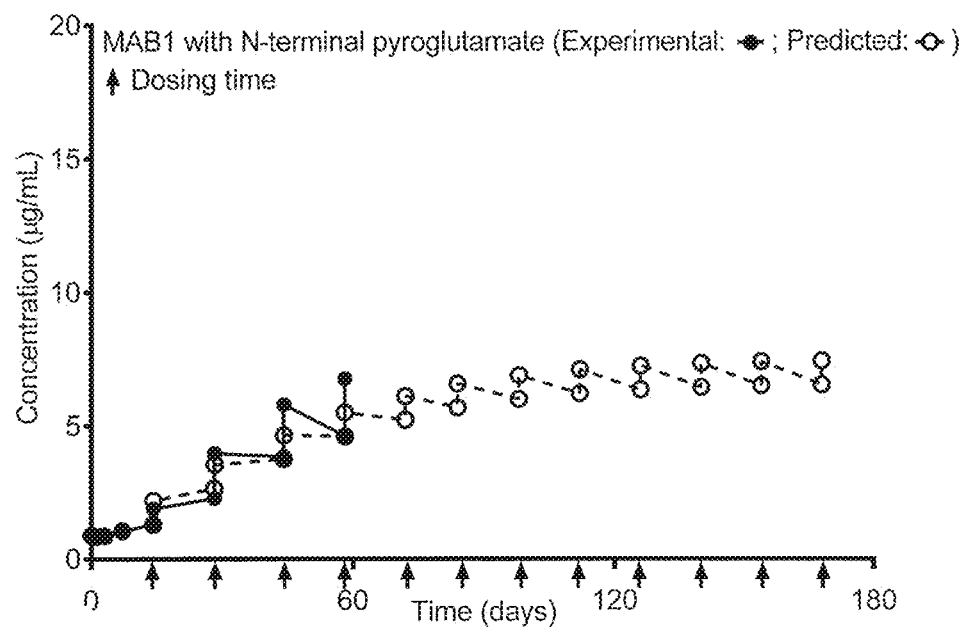
FIG. 10A is a graph showing model predictions and experimental measurements of the serum concentration of MAB1 with N-terminal pyroglutamate from the multiple-dose PK study. The predicted pre-dose and post-dose serum concentrations of MAB1 with N-terminal pyroglutamate are in good agreement with the experimental measurements. The pre-dose and post-dose concentrations of MAB1 with N-terminal pyroglutamate approach the steady-state levels following an extended period of dosing.

The predicted and experimentally determined subject's exposure to MAB1 with N-terminal pyroglutamate over the course of 5 doses (56 days) were 218.5 µg/mL·day and 231.8 µg/mL·day, respectively (FIG. 10A). The predicted and experimentally determined subject's exposure to MAB1 with N-terminal pyroglutamate as a fraction of the subject's exposure to total MAB1 over 56 days were 4.3% and 4.8%, respectively.

Figure 9B:
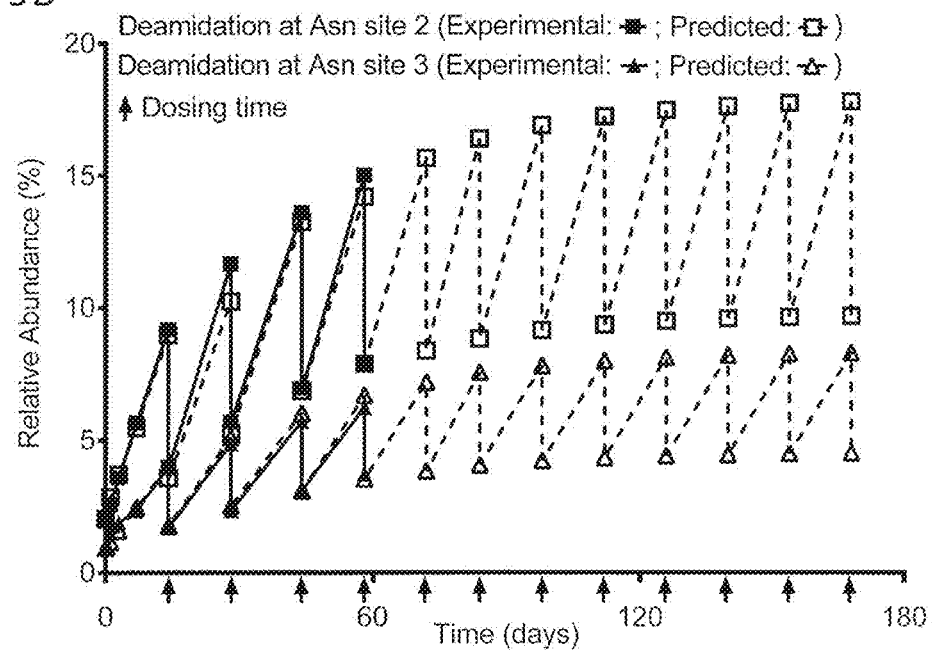
FIG. 9B is a graph showing model predictions and experimental measurements of the relative abundances of deamidation at Asn site 2 or Asn site 3. The predicted levels are in good agreement with the experimental values. The pre-dose and post-dose relative abundances of deamidation at Asn site 2 or Asn site 3 approach the steady-state levels following an extended period of dosing. Each dosing time is indicated with an arrow "↑".

Modeling the In Vivo Relative Abundances of the MAB1 PQAs in the Multiple-Dose Study The models can also be used to predict the pre-dose and post-dose levels of a PQA of a mAb at any given dose during a multiple-dose study using Equation 12 and Equation 13, respectively. For example, the predicted pre-dose and post-dose levels of deamidation at Asn site 2 on Day 56 are 14.2% and 7.9%, respectively. The predicted values are consistent with the LC/MS determined pre-dose and post-dose on Day 56, which were 15.0% and 7.9%, respectively. All other predicted levels of deamidation (FIG. 9B, hollow circles) are in good agreement with the experimental measurements (FIG. 9B, solid dots). The pre-dose and post-dose PTM levels in a multiple-dose study will reach a steady state as the pre-dose and post-dose mAb serum concentrations reach the steady-state concentrations (FIG. 9B). The predicted pre-dose and post-dose steady-state levels of an PQA (i.e., the plateau levels) correspond to the maximum and minimum levels of this PQA in vivo in a multiple-dose study. Using Equation 16 and Equation 17, the pre-dose and post-dose steady-state levels of MAB1 with deamidation at Asn site 2 were determined to be 17.9% and 9.7%, respectively.

Similarly, the predicted pre-dose and post-dose levels of deamidation at Asn site 3 (FIG. 9B, hollow triangles) are in good agreement with the experimental measurements (FIG. 9B, solid triangles). The pre-dose and post-dose steady-state levels of MAB1 with deamidation at Asn site 3 were determined to be 8.4% and 4.6%, respectively.

Figure 10B:
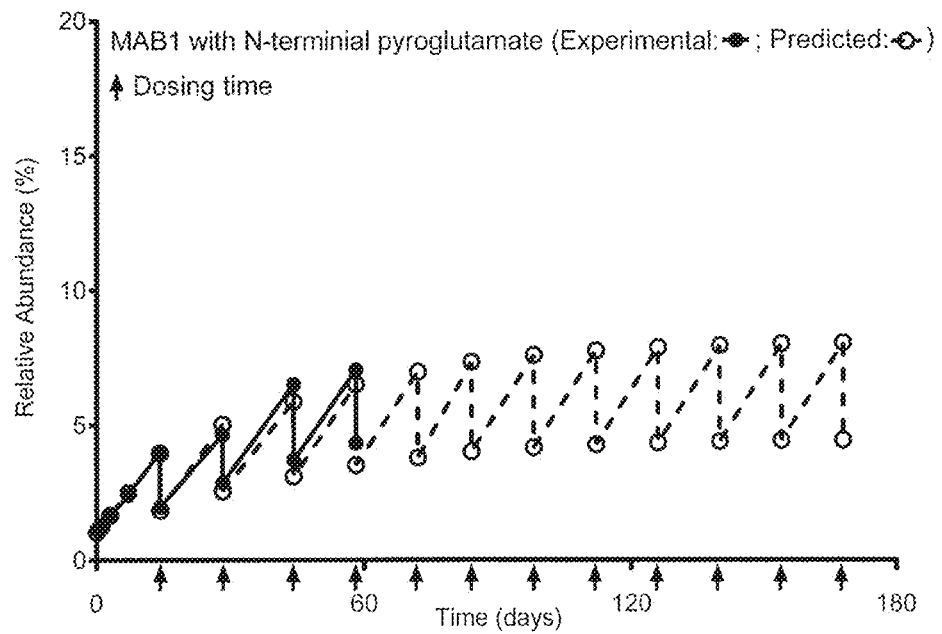
FIG. 10B is a graph showing model predictions and experimental measurements of the relative abundances of N-terminal pyroglutamate. The predicted levels are in good agreement with the experimental values. The pre-dose and post-dose relative abundances of N-terminal pyroglutamate approach the steady-state levels following an extended period of dosing. Each dosing time is indicated with an arrow "↑".

The predicted pre-dose and post-dose levels of N-terminal pyroglutamate (FIG. 10B, hollow circles) are in good agreement with the experimental measurements (FIG. 10B, solid dots). The pre-dose and post-dose steady-state levels of MAB1 with N-terminal pyroglutamate were determined to be 8.1% and 4.5%, respectively.

Example Applications of the Models

Figure 11A:
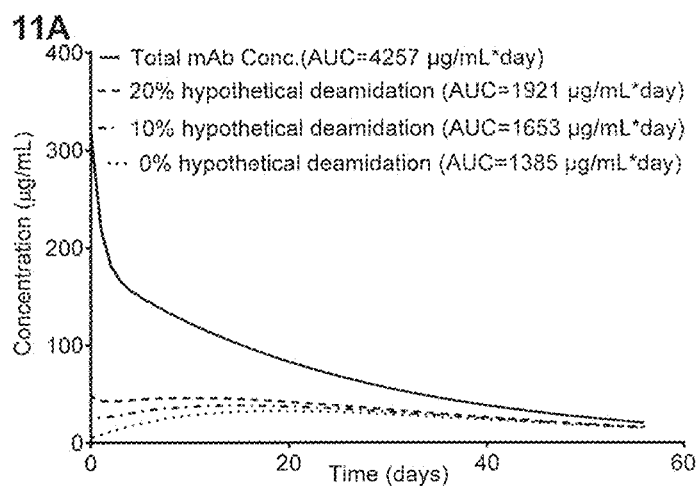
FIGS. 11A and 11B are graphs showing modeling of the subject's exposure to a hypothetical CDR deamidation with an in vivo deamidation rate of 2.5% per day$^{-1}$ and initial deamidation levels at 0%, 10%, and 20% in the single-dose study (FIG. 11A) and the multiple-dose study (FIG. 11B).
Figure 11B:
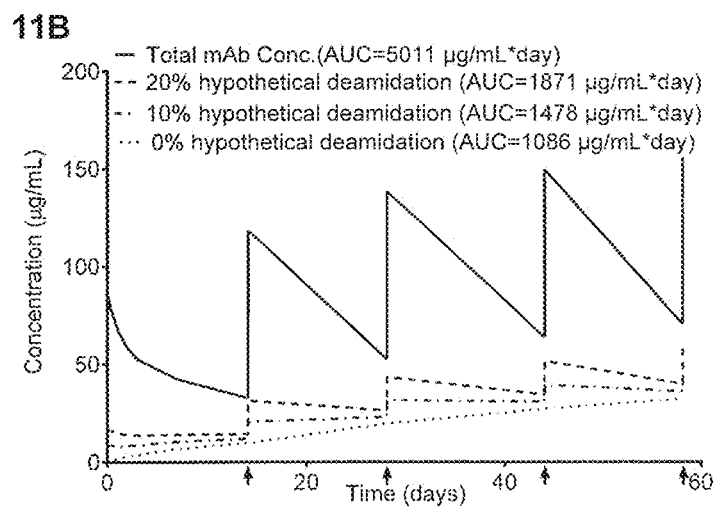

Quantitative assessment of PQAs of a therapeutic protein in vivo is important because it helps to identify potential critical quality attributes (CQAs) that would not otherwise be identified in vitro, thereby influencing product risk assessment and control strategy. The models described in this paper can be used to quantitatively assess of PQAs in many applications. First, the in vivo progression of PQAs and the subject's exposure to the PQAs in single and multiple-dose regimens can be calculated using these models. The good agreements between model predictions and experimental measurements have been demonstrated in the sections above (FIGS. 8, 9, and 10). Second, the models can be used to predict the subject's exposure by extending the dosing period (t) and determine the pre-dose and post-dose steady-state concentrations/levels of PQAs (FIGS. 9 and 10), providing insights to pre-clinical and clinical studies. Third, the models can be used to evaluate the impact of changes in the initial levels of PQAs resulting from process changes or lot-to-lot variability by adjusting the initial levels of PQAs ($P_0$) in the modeling equations. This is particularly meaningful if the PQA is a CDR modification. Since the MAB1 used in this work does not have a CDR modification suitable for this modeling application, a hypothetical CDR deamidation with an in vivo deamidation rate of 2.5% per $day^{-1}$ was used as an example of using the models to assess the impact of the initial levels of CDR deamidation on the subject's exposure to PQAs. If there were three batches of drug products with the initial levels of the hypothetical CDR deamidation of 0%, 10%, and 20%, respectively. The hypothetical CDR deamidation in vivo overtime of these batches can be described as $P_{deam}(t)=1-(1-0)\cdot e^{-0.025t}$, $P_{deam}(t)=1-(1-0.1)\cdot e^{-0.025t}$, and $P_{deam}(t)=1-(1-0.2)\cdot e^{-0.025t}$, respectively. Using the models described above, the subject's exposure to the hypothetical CDR deamidated variants with 0%, 10%, and 20% initial deamidation over 56 days in the single-dose study are 1385 µg/mL·day, 1653 µg/mL·day, and 1921 µg/mL·day, respectively, consisting of 32.5%, 38.8%, and 45.1% subject's exposure to the total mAb, respectively (FIG. 11A). For multiple-dose study, the subject's exposure to the hypothetical CDR deamidated variants with 0%, 10%, and 20% initial deamidation over 5 doses (56 days) are 1086 µg/mL·day, 1478 µg/mL·day, and 1871 µg/mL·day, respectively, consisting of 21.7%, 29.5%, and 37.3% subject's exposure to the total mAb, respectively (FIG. 11B). Thus, if the process control resulted in ±10% of initial levels of this hypothetical CDR deamidation, the subject's exposure to this CDR deamidated mAb varies about 6-8% in the single- or multiple-dose studies over 56 days. Since the modeling demonstrates that the subject's exposure to this hypothetical CDR deamidation is insensitive to the initial level of the PQA, the acceptable ranges of the PQA could be widened to allow justification of process risk assessment. Combining with the effect of a CDR modification on the potency measured by a potency assay, the modeling results can be used to estimate the subject's exposure to effective drug when the initial CDR modification changes resulted from process controls or lot-to-lot variation, providing critical information for product risk assessment.

DISCUSSION

The dynamic in vivo environment of the circulating bloodstream, resulting in mAb clearance, elimination, and degradation, is much more relevant for assessing changes of PQAs in patients compared to the static incubation of mAbs in PBS or serum in vitro (Yin et al., Pharmaceutical research 2013; 30:167-78). Thus, in vivo PQA quantitation and modeling provide critical information, which would not obtain from the in vitro studies, to assess the criticality of the PQAs. For example, For example, these results presented herein (FIG. 6) and previous studies (Li et al., mAbs 2016:0; Cai et al., Biotechnology and Bioengineering 2011; 108: 404-12) have shown that in vivo C-terminal lysine is rapidly removed within one day. Similarly, trisulfide bonds have been shown to be rapidly converted to disulfide bonds in vivo (Li et al., mAbs 2016:0). The results presented herein (FIG. 4) and previous studies (Li et al., mAbs 2016:0; Li et al., mAbs 2016:0) demonstrated that the levels of methionine oxidation are often unaffected following in vivo administration. Therefore, C-terminal lysine removal, trisulfide bond, and methionine oxidation are less likely to be considered CQAs. In contrast, deamidation were shown to accumulate in vivo in single- and multiple-dosing regimens (FIG. 3) and previous studies (Li et al., mAbs 2016:0; Li et al., mAbs 2016:0). Deamidation that occurs and accumulates at the CDR region could potentially impact on drug efficacy (Yan et al., Journal of pharmaceutical sciences 2009; 98:3509-21; Haberger et al., mAbs 2014; 6:327-39) or cause off-target binding. Thus, modeling CDR deamidation in vivo using the equations described in this paper can quantitatively assess the impact of the CDR deamidation on the subject's exposure, as demonstrated above (FIG. 11).

In this work, asparagine deamidation and N-terminal pyroglutamate formation were used as representative PTMs to demonstrate the validity of our models. Our models can also be applied to other PTMs that exhibit either increasing or decreasing trends. For example, models were applied to assess Mannose 5 clearance by adopting the third-order kinetic because of the enzymatic based clearance of Mannose 5. The predicted values matched well with the experimental data even though the relative abundance of Mannose 5 decreased to below 1.0% over time (data not shown). Our models can be used to calculate other parameters to evaluate a given attribute or PTM in a multiple-dose study. These parameters include the accumulation rate to the steady state, the average level at the steady state, and the degree of variability of a PTM at the steady state.

In summary, the inventors characterized the common in vivo PTM changes of a therapeutic mAb (MAB1), and modeled the in vivo behaviors of PTMs for both single- and multiple-dose studies regimens to evaluate the impact of in vivo PTMs. Three asparagine residues located in the Fc region of MAB1 exhibited different deamidation rates. The levels of oxidation at three methionine residues in the Fc region of MAB1 showed no change over time in vivo. N-terminal pyroglutamate formed rapidly in vivo. C-terminal lysine was completely removed within one day. MAB1 possessing high mannose glycosylation revealed the accelerated clearance. We used two Asn deamidation and the N-terminal pyroglutamate formation as representative PQAs and built modeling equations to calculate the serum concentrations of PQAs, the subject's exposure to PQAs, and the in vivo relative abundances of PQAs both single- and multiple-dose regimens. The model predictions were validated by the experimental measurements. Thus, the models can be used to simulate the in vivo PQA progression subject's exposure to PQAs in both single- and multiple-dose regimens providing quantitative approaches for the criticality assessment PQAs in therapeutic mAbs.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method of determining criticality of a product quality attribute (PQA) of an antibody after multiple administrations of the antibody to a subject, comprising:
 (a) predicting an in vivo serum concentration of the antibody with a PQA after a single administration of the antibody by:
  (i) predicting a percentage of the antibody with the PQA using an in vivo rate constant determined for the PQA; and
  (ii) multiplying the predicted percentage of the antibody with the PQA by a total in vivo concentration of the antibody to determine the concentration of the antibody with the PQA and thereby producing a single-administration model;
 (b) repeating step (a) at least once and thereby producing one or more additional single-administration models;
 (c) superimposing the single-administration models of steps (a) and (b) and thereby producing a multiple-administration model; and
 (d) using the multiple-administration model to determine the criticality of the PQA,
 wherein the PQA includes a post-translational modification of interest.

2. The method of claim 1, wherein the in vivo rate constant for the post-translational modification is determined by quantitating a percentage of the post-translational modification of interest as a function of time and fitting the quantitated percentage of the post-translational modification of interest to the equation $P_{PTM}(t)=1-(1-P_0)\cdot e^{-k_{PTM}t}$, where $P_{PTM}(t)$ is the proportion of the post-translational modification as a function of time; $P_0$ is an initial percentage post-translational modification; and $k_{PTM}$ is the post-translational modification rate constant.

3. The method of claim 1, further comprising determining an exposure of the subject to the antibody with the post-translational modification of interest, wherein determining an exposure of the subject to the antibody with the post-translational modification of interest comprises determining the area under the curve (AUC) of the concentration of the antibody with the post-translational modification of interest.

4. The method of claim 1, wherein the serum concentration of the antibody is described by a two-compartment pharmacokinetic model equation as $C(t)=Ae^{-\alpha t}+Be^{-\beta t}$, where A and B are hybrid coefficients when $\alpha$ and $\beta$ are hybrid first order constants, respectively.

5. The method of claim 1, wherein the antibody comprises a recombinant therapeutic monoclonal antibody.

6. The method of claim 1, wherein the PQA can impact drug stability, safety, and/or efficacy.

7. The method of claim 1, wherein the method is used to predict or monitor the post-translational modification profile of an antibody.

8. The method of claim 1, wherein the post-translational modification comprises one or more of deamidation, oxidation, glycation, disulfide formation, N-terminal pyroglutamate formation, C-terminal lysine removal, and high mannose glycosylation.

9. The method of claim 1, further comprising:
   (i) modeling a correlation between [PK] pharmacokinetic concentration and proportion of post-translational modification variants;
   (ii) quantitatively assessing and predicting the subject exposure to a representative post-translational modification in either a single-dose regimen or a multiple-dose regimen;
   (iii) predicting a maximum and a minimum post-translational modification level observed in a multiple-dose regimen;
   (iv) administering the antibody to the subject; and/or
   (v) determining a total in vivo concentration of the antibody in the subject.

10. The method of claim 1, further comprising predicting a pre-dose in vivo concentration of an antibody with the post-translational modification of interest.

11. The method of claim 1, further comprising predicting a post-dose in vivo concentration of an antibody with the post-translational modification of interest.

* * * * *

UNITED STATES PATENT AND TRADEMARK OFFICE
CERTIFICATE OF CORRECTION

PATENT NO. : 11,355,217 B2
APPLICATION NO. : 16/264044
DATED : June 7, 2022
INVENTOR(S) : Xiaobin Xu et al.

It is certified that error appears in the above-identified patent and that said Letters Patent is hereby corrected as shown below:

On the Title Page

(73) Assignee, Line 1, should read:
Regeneron Pharmaceuticals, Inc.

In the Claims

Column 30, Lines 6-9, (Claim 9) should read:
The method of claim 1, further comprising:
(i) modeling a correlation between pharmacokinetic concentration and proportion of post-translational modification variants;

Signed and Sealed this
First Day of November, 2022

Katherine Kelly Vidal
*Director of the United States Patent and Trademark Office*